US009757228B2

United States Patent
Wanders et al.

(10) Patent No.: US 9,757,228 B2
(45) Date of Patent: *Sep. 12, 2017

(54) OPHTHALMIC LENS WITH OPTICAL SECTORS

(71) Applicant: OCULENTIS HOLDING B.V., Eerbeek (NL)

(72) Inventors: Bernardus Franciscus Maria Wanders, Angerlo (NL); Walter Bernardus Johannes Wolterinck, Arnhem (NL)

(73) Assignee: OCULENTIS HOLDING B.V., Eerbeek (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/184,791

(22) Filed: Feb. 20, 2014

(65) Prior Publication Data

US 2014/0172091 A1   Jun. 19, 2014

Related U.S. Application Data

(63) Continuation of application No. 13/201,800, filed as application No. PCT/NL2010/050078 on Feb. 17, 2010, now Pat. No. 8,696,746.

(Continued)

(30) Foreign Application Priority Data

Feb. 17, 2009  (NL) .................................... 2002540

(51) Int. Cl.
  *A61F 2/16*  (2006.01)
  *G02C 7/04*  (2006.01)
  *G02C 7/02*  (2006.01)

(52) U.S. Cl.
  CPC .......... *A61F 2/1618* (2013.01); *A61F 2/1602* (2013.01); *G02C 7/04* (2013.01);
  (Continued)

(58) Field of Classification Search
  CPC .... A61F 2/1602; A61F 2/1618; A61F 2/1637; A61F 2250/0026; A61F 2250/0014;
  (Continued)

(56) References Cited

U.S. PATENT DOCUMENTS 4,484,804 A   11/1984  Mignen
4,637,697 A *  1/1987  Freeman .............. G02B 5/1876
                                                351/159.44

(Continued)

FOREIGN PATENT DOCUMENTS

CN         1171557 A    1/1998
CN       101208628 A    6/2008
(Continued)

*Primary Examiner* — Paul Prebilic
(74) *Attorney, Agent, or Firm* — Sughrue Mion, PLLC

(57) ABSTRACT

An ophthalmic lens comprising a main lens part, a recessed part, an optical center, and an optical axis through the optical center. The main lens part has at least one boundary with the recessed part and has an optical power of between about −20 to about +35 diopter. The recessed part is positioned at a distance of less than 2 mm from the optical center and includes a near part having a relative diopter of about +1.0 to about +5.0 with respect to the optical power of the main lens part. The boundary or boundaries of the recessed lens part with the main lens part form a blending part or blending parts, are shaped to refract light away from the optical axis, and have a curvature resulting in a loss of light, within a circle with a diameter of 4 mm around the optical center, of less than about 15%.

17 Claims, 14 Drawing Sheets

Related U.S. Application Data

Figure 1:
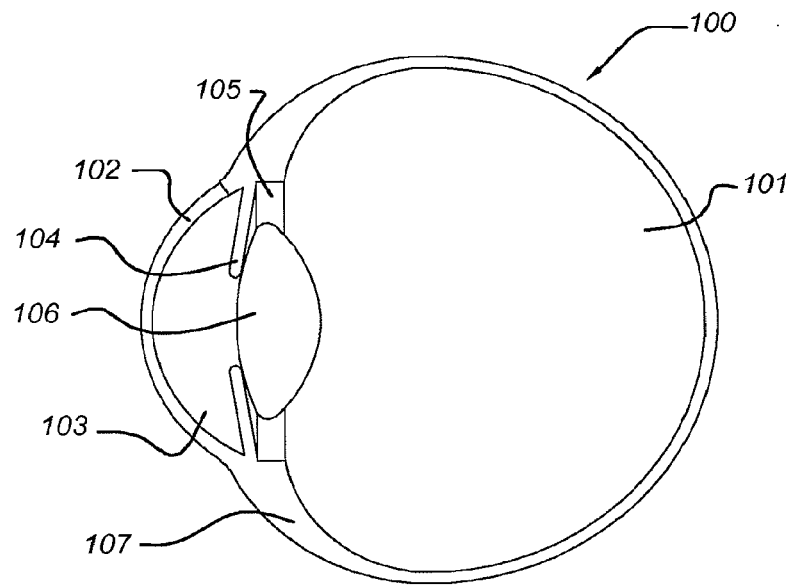

(60) Provisional application No. 61/153,044, filed on Feb. 17, 2009.

(52) U.S. Cl.
CPC ............. *G02C 7/042* (2013.01); *G02C 7/045* (2013.01); *G02C 7/028* (2013.01)

(58) Field of Classification Search
CPC ...... A61F 2250/0036; A61F 2250/0037; A61F 2250/0053; A61F 2250/0091; G02C 7/045; G02C 7/04; G02C 7/042; G02C 7/028; G02C 7/06; G02C 2202/00; G02C 2202/04; G02C 2202/06; G02C 2202/20; G02C 2202/22
USPC ........ 623/6.24–6.34, 5.11, 5.14; 351/159.35, 351/159.44, 159.05–159.15
See application file for complete search history.

(56) References Cited

U.S. PATENT DOCUMENTS

| | | | |
|---|---|---|---|
| 4,769,033 A * | 9/1988 | Nordan | A61F 2/1618 623/6.24 |
| 4,952,045 A * | 8/1990 | Stoyan | A61F 2/14 351/159.1 |
| 5,089,023 A * | 2/1992 | Swanson | A61F 2/1618 359/565 |
| 5,391,202 A * | 2/1995 | Lipshitz | A61F 2/1648 623/6.34 |
| 5,652,014 A | 7/1997 | Galin et al. | |
| 6,092,899 A * | 7/2000 | Wanders | G02C 7/043 351/159.48 |
| 6,220,705 B1 | 4/2001 | Francois et al. | |
| 6,409,339 B1 * | 6/2002 | Wanders | G02C 7/043 351/159.48 |
| 6,793,340 B1 | 9/2004 | Morris et al. | |
| 7,004,585 B2 | 2/2006 | Lindacher | |
| 8,444,267 B2 * | 5/2013 | Weeber | A61F 2/1618 351/159.35 |
| 8,696,746 B2 * | 4/2014 | Wanders | A61F 2/1602 351/159.15 |
| 2002/0075446 A1 | 6/2002 | Lossman et al. | |
| 2004/0207807 A1 | 10/2004 | Lindacher | |
| 2004/0257526 A1 | 12/2004 | Lindacher | |
| 2005/0128432 A1 | 6/2005 | Altmann | |
| 2007/0182924 A1 | 8/2007 | Hong et al. | |
| 2009/0046349 A1 * | 2/2009 | Haddock | G02B 5/1895 359/319 |
| 2011/0317124 A1 * | 12/2011 | Weeber | A61F 2/1618 351/159.11 |
| 2012/0029631 A1 | 2/2012 | Wanders et al. | |

FOREIGN PATENT DOCUMENTS

| | | |
|---|---|---|
| CN | 101506717 A | 8/2009 |
| JP | H11-514753 A | 12/1999 |
| JP | 2006-517305 A | 7/2006 |
| JP | 2006-523855 A | 10/2006 |
| WO | 97/16760 A1 | 5/1997 |
| WO | 2008/007955 A1 | 1/2008 |
| WO | WO 2008/007955 A1 * | 1/2008 ............. G02C 7/041 |

* cited by examiner

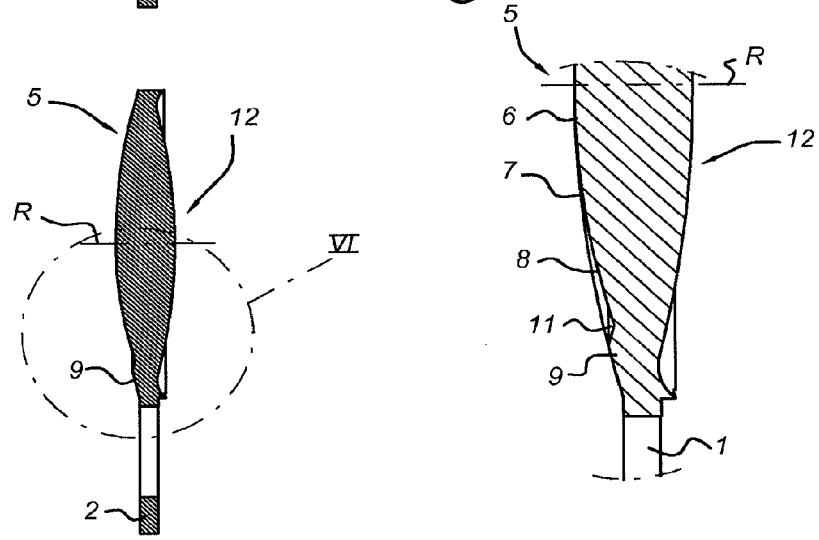

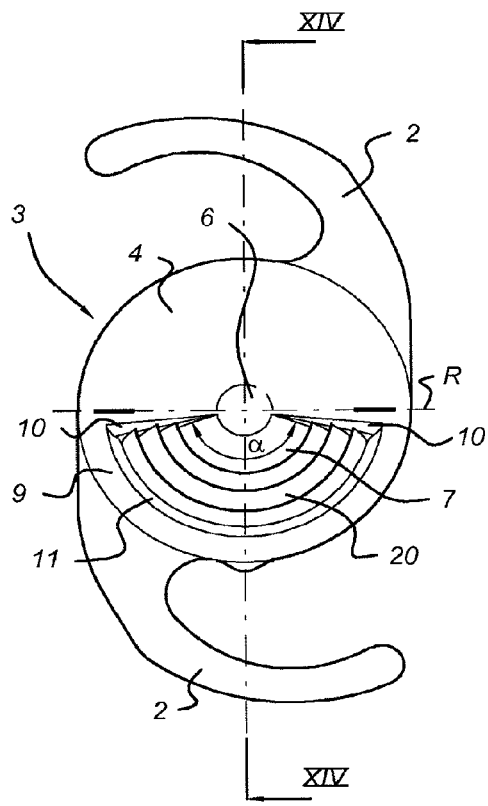
Fig 12
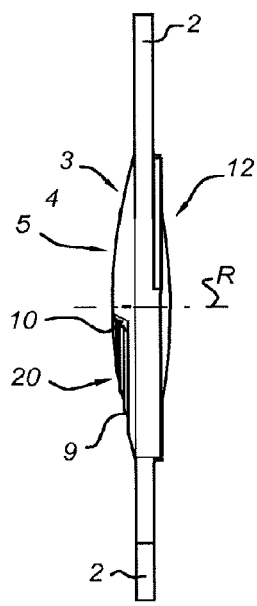
Fig 13
Fig 14

OPHTHALMIC LENS WITH OPTICAL SECTORS

CROSS REFERENCE TO RELATED APPLICATIONS

This is a Continuation application of U.S. application Ser. No. 13/201,800 filed Oct. 18, 2011now U.S. Pat. No. 8,696,746, which is a National Stage of International Application No. PCT/NL2010/050078 filed Feb. 17, 2010, claiming priority based on NL Patent Application No. 2002540 filed Feb. 17, 2009, and U.S. Provisional Patent Application No. 61/153,044 filed Feb. 17, 2009, the contents of all of which are incorporated herein by reference in their entirety.

BACKGROUND

The present invention relates to an ophthalmic lens comprising a main lens part and a recessed part.

One particular type of ophthalmic lenses of that type is an Multifocal Intra Ocular Lens (MIOL). It usually comprises a lens part with a centre, which lens part is provided on the periphery with supporting parts (haptics). Lenses of this type are generally known in the state of the art. These are used for replacement of the eye lens after cataract operations, for example many attempts are made to provide MIOL with concentric annular optical zones for reading distance and or intermediate vision. In a "simultaneous vision multifocal", the relationship between the distance zone and the near zone is quite critical. In order for that type of lens to function properly, it must permit approximately equal amounts of light into the eye through both the near zone and the distance zone. This is required so that vision is not biased toward either vision correction. Obviously, because of the great variation in light levels in daily life, which accordingly change the diameter of the pupil, a compromise must be reached upon when selecting the size of each zone. This problem, also refers to as "pupil dependency", is further complicated as the difference in pupil size varies substantially from patient to patient. Examples of these types of lenses may be seen in U.S. Pat. Nos. 4,636,049; 4,418,991; 4,210,391; 4,162,172; and 3,726,587, and in patent application US 2006/0212117, EP0590025B1, U.S. Pat. No. 6,126,286. Another problem of those annular concentric designed MIOL are the ghost images and blur due to the light directed to the macula at the annular zone transitions. Another big drawback of current MIOL is the loss of contrast sensitivity. Contrast sensitivity determines the lowest contrast level which can be detected by a patient for a given size target. Normally a range of target sizes are used. In this way contrast sensitivity is unlike acuity. Contrast sensitivity measures two variables, size and contrast, while acuity measures only size. Contrast sensitivity is very similar to auditory testing, which determines a patient's ability to detect the lowest level of loudness of various sound frequencies. The patient is asked to depress a button when the tone is just barely audible and release the button when the tone can no longer be heard. This procedure is used to test auditory sensitivity to a range of sound frequencies. If auditory testing were evaluated in a similar way to visual acuity, all the sound frequencies would be tested at one high level of loudness.

The problem of pupil dependency of simultaneous vision multifocal performance is claimed to be diminished by a further embodiment of simultaneous vision multifocals that operates under the principles of diffraction. Examples of these types of lenses were presented in U.S. Pat. Nos. 4,641,934 and 4,642,112. Due to the nature of diffractive optics, at least 20% of the incoming light will be lost and patients suffer from halos and glare.

To solve this pupil independency several attempts have been made, such as disclosed in U.S. Pat. No. 4,923,296 which describes a lens divided into a series of substantially discrete near and distant vision zones. Not clear from this disclosure is how these vision zones could be made and or joined together. WO 92/06400 describes a aspheric ophthalmic lens. The surface zones are defined three dimensionally forming a junctionless, continuous and smooth surface in conjunction with one another. It will be clear to a person skilled in the art that such a lens will suffer a large decrease of optical quality. U.S. Pat. No. 4,921,496 describes a rotation symmetric, radially segmented IOL. That IOL has no junctions at the surface, since the materials for each segment should have different refractive indices to create the different powers.

Another lens with a distance part and a near part is described in EP0858613(B1) and U.S. Pat. No. 6,409,339 (B1) by Procornea Holding B.V. from the current inventor, and which are incorporated by reference as if fully set forth. These documents disclose contact lenses, but also refer to IOL's. A lens of this type differs from other lenses in that the reading part is located within the (imaginary) boundary of the distance part. That is to say the reading part is on or within the imaginary radius of the outer boundary of the distance part (Rv). If a reading part is used this is preferably made as a sector which extends from the centre of the lens. This lens proved to have many possibilities. There is, however, room for further improvement.

It has been found after extensive clinical testing that for a MIOL as disclosed in U.S. Pat. No. 6,409,339(B1), the transition profile used to bridge the step height between the sector boundaries is not optimal. This results in reduction of the usable optical area and significant loss of light energy and contrast sensitivity. The optical configuration as disclosed herein provides a distinct bifocal image whereas a multifocal image is necessary to reduce halo's with big pupil size and at the same time have a clear vision with high contrast at near and intermediate distance. EP0858613(B1) and U.S. Pat. No. 6,409,339(B1) in particular discloses that the transitions should be smooth and have a sigmoid or sine shape curve to bridge the step height difference between both optical parts. U.S. Pat. No. 6,871,953, to Mandell, published September 2003, surprisingly discloses the same use of sigmoid curve types to bridge the step height resulting in exactly the same lens configuration as described in EP0858613 (B1). The purpose of the sigmoid curves in both applications when relating to contact lenses is to make the transitions between the optical parts as smooth as possible to reduce friction of the eyelid. A drawback of the wide transitions described therein is that it also creates a high loss of light energy and was found to reduce contrast sensitivity. U.S. Pat. No. 6,871,953 discloses to make the transitions wider to create even smoother transitions. Due to the alternating principle of a contact lens, the contact lens nowadays moves up on the eye when line of sight is down gaze. The loss of light at the transitions under these alternating conditions for contact lenses is not determined. The opposite, however, is true for a MIOL. Such a lens is fixed in the eye. The optical usable area of the semi-meridian sectors will be reduced, which leads to less light energy being directed to the macula. This results in poor optical performance either for distance or near vision. Furthermore it has been found that due to the fact that the pupil size varies under different light conditions, unwanted halo effects may occur with big pupil size. Therefore it would be beneficial to have a apodized power profile in the reading part to reduce this phenomenon and introduce multifocallity at same moment.

U.S. Pat. No. 7,004,585 discloses a multifocal contact lens having a blended design for a segmented optical zone. The contact lens should move on the eye easily in order to make the lower reading zone available. Furthermore, a transition or blend zone should be designed to avoid blur and ghost images. To that end, the blend zone should have a smooth transition to improve wearers comfort. Furthermore, the blend zone should include a curvature magnitude to refract light away from the macular region of the eye. The various optical zones should influence each other as little as possible. In this document, patentee seems to have identified that problem. The solution of making the blend zone as smooth as possible and providing a reading zone in a particular way, however, seems complex. The ophthalmic lens design can be further improved, however. In particular for IOL devices, there is room for further improvement.

In U.S. Pat. No. 7,237,894, a ophthalmic lens was designed with a radial centre below the centre of the optical zone. In that way, however, it is difficult to avoid an image shift.

SUMMARY OF THE INVENTION

At least some of the disadvantages of the prior art illustrated above are overcome by the present invention.

To that end, the invention provides an ophthalmic lens comprising a main lens part having a surface, a recessed part having a surface which is recessed with respect to said surface of said main lens part, an optical centre, and an optical axis through said optical centre, said main lens part having at least one boundary with said recessed part, said main lens part having an optical power of between about −20 to about +35 dioptre, said recessed part positioned at a distance of less than 2 mm from said optical centre and comprising a near part having a relative dioptre of about +1.0 to about +5.0 with respect to the optical power of said main lens part, said boundary or boundaries of said recessed lens part with said main lens part form a blending part or blending parts, are shaped to refract light away from said optical axis and have a curvature resulting in a loss of light, within a circle with a diameter of 4 mm around said optical centre, of less than about 15%, said loss of light defined as the fraction of the amount of in-focus light from the IOL compared to the amount of in-focus light from an identical IOL without said recessed part.

This ophthalmic lens allows various optical parts to be integrated in one single lens in such a way that they influence one another as little as possible. For instance, it allows an ophthalmic lens with a reading part is such a way that distance vision, intermediate vision and near vision influence each other little to not. In fact, it was found that we were able to significantly increase contrast sensitivity of ophthalmic lenses. In the past a lens would be designed to cause as little disturbance as possible. In the current invention, it was found that sharp transitions can be allowed, as long as they cause light to be refracted away from the optical axis. In fact, as long as these sharp transitions cause the lens to refract less than 15% of the light way from the optical axis, this would result in for instance an IOL which provides improved contrast sensitivity and vision. This loss of light is in fact defined for a pupil diameter of 4 mm.

In this respect, light is defined as light in the visual wavelength range. Usually this is between about 400-700 nm.

The amount of in-focus light is the sum of focussed light in all the main focal planes of the IOL. Thus, if for instance the central part has relative dioptre 0, and the recessed part has a relative dioptre with respect to the main lens part, the lens will usually have two focal planes, one for the main lens part and one for the recessed part. If the optical area of the recessed part is 30% of the entire lens area and the area of the main lens part is 70%, and there is no further loss, then 30% of the focussed light will be available in the focal plane of the recessed part and 70% of the focussed light will be available in the focal plane of the main lens part.

In an embodiment, the lens comprises at least one recessed, semi-meridian optical sector which is radially and/or angularly subdivided into subzones. It thus may comprise an inner sector, an intermediate sector, and an outer sector, located within the (imaginary) boundary of the lens part. The inner sector has a first optical power, the intermediate sector which is adjacent to the inner sector has a second optical power. The outer sector adjacent to the intermediate sector has a third optical power. The step height between the boundaries of the semi-meridian sectors are joined by means of an optimised transition profile to maximize light energy directed to the macula and to reduce blur and halo's at bigger pupil sizes. The ophthalmic lens semi-meridian sectors can have a continuous power profile. Alternatively, the optical sub circle sectors are blended together. Combinations thereof are also possible. The subdivided sector(s) will provide a clear vision at reading and intermediate distances, whereas the distance vision and contrast sensitivity remain comparable with an monofocal ophthalmic lens.

The present invention may also be configured to provide lenses which perform well in eyes with varying corneal aberrations (e.g., different asphericalities), including spherical aberration, over a range of decentralization, i.e. deviation between the optical axis or centre of the lens and the optical axis of the eye. This means that positioning of the IOL becomes less critical.

In an embodiment, the ophthalmic lenses of the invention may comprise more than three subdivided semi-meridian or semi-meridian sector zones.

In a further embodiment of the invention the opposite surface of the lens may comprise an aspheric surface such that the residual spherical aberration will be reduced to about zero. For instance such as described in, but not limited to EP1850793, 1857077 or US2006279697 incorporated herein by reference.

In a further embodiment of the invention the semi-meridian recessed refractive reading part can comprise boundaries at all sides, and may even comprises an additional diffractive optical element (DOE) structure, for instance such as described in, but not limited to, EP0888564B1 or EP1194797B1, incorporated herein by reference.

Another object of the invention is to provide a method and optimized curves to optimise and improve the steepness of the transition profile to bridge height differences between parts of the lens. These blending parts improved the transition between various parts. Using these blending parts will reduce loss of light energy and maximizes the usable optical area(s) significantly. The step height differences at for instance semi-meridian boundaries may be bridged by methods using a cosine trajectory or sigmoid function. In an embodiment, however, optimised transition function are proposed. These derived transition functions consistent with the outcome of the optimised profile function are consistent with the embodiments of the invention.

The dimension and/or optical power ratio between various parts, for instance a semi-meridian subdivided reading part and a distance part, may mutually vary. If two lenses are used, for both eyes of the patient, one lens can be configured for the dominant eye and the other lens for the non-dominant eye. That is to say, the lens for one eye has a different configuration for the reading part or distance part than the lens for the other eye.

It is also known that there is a functional dependence between pupil size and luminance. For example, such data was reported in Glen Myers, Shirin Berez, William Krenz and Lawrence Stark, Am. J. Physiol. Regul. Integr. Comp. Physiol, 258: 813-819 (1990). Pupil size is a function of the weighted average of the luminances (popularly called brightness) within the field of view. Pupil size is influenced much more by the part of the retina associated with central, or foveal, vision than by the outer areas of the retina.

The following listing presents some levels of field brightness and associated "typical" conditions

| Field brightness (cd/m2) | Condition |
| --- | --- |
| 30 | Subdued indoor lighting |
| 60 | Less than typical office light; sometimes recommended for display-only workplaces |
| 120 | Typical office |
| 240 | Bright indoor office |
| 480 | Very bright; precision indoor tasks |
| 960 | Usual outdoors |
| 1920 | Bright afternoon |

A customized recessed semi-meridian lens could be designed by using certain field brightness conditions to calculate the optimal central part and or reading part in relation to the specific pupil diameter.

Apart from the corrective distance sector and semi-meridian subdivided near sector described above, further corrections can be made in the lens sectors to optimize or correct particular optical abnormalities. It should be understood that a further structure, which makes it possible to correct all kinds of optical abnormalities, such as but not limited to astigmatism and spherical aberration, can be arranged at the anterior or posterior side of the current lens.

The recessed part, for instance formed as a semi-meridian reading sector, is positioned in the eye in an embodiment at the lower part or bottom (inferior) of the lens because this corresponds to the natural inclination of people to look down when reading. However, the positioning of the semi-meridian reading sector in the eye is not critical and can be positioned Superior, Inferior, Nasal or Temporal. Distant and near sectors can even be disposed in opposite arrangement for the two eyes of one person.

The ophthalmic lens or mould described herein can be made in any way known in the art. For an intraocular lens, for instance, it is in addition possible to make the lens part and the haptic separately and to connect them together later. However, it is also possible to make them as one entity. According to an embodiment, these parts are made as one entity by (injection) moulding. A subsequent processing for producing the proper lens parts can be turning. As described in U.S. Pat. No. 6,409,339B1, during such a turning operation a tool bit can be moved every revolution towards and away from the lens in the direction parallel to the rotational axis. This makes it possible to produce the lens part by turning. It is also possible according to an embodiment to perform the turning so finely that a subsequent polishing operation can be omitted. The material of the lens can be any desired material.

The novel ophthalmic lens optic configuration for example can also be used for contact lenses and for pseudophakic intra-ocular lens patients as a so called "add on lens". This is an extra or additional lens which can be placed in front of a existing natural lens or in front of a artificial intra ocular lens to correct refraction errors and or to restore reading capabilities. The add-On lens could be placed in the bag, the sulcus, as cornea inlay or as a anterior chamber lens.

With modern lens power mapping apparatus, such as the High resolution Hartmann Shack system "SHSInspect Ophthalmic", commercial available from Optocraft Germany, it is possible to determine the local refractive powers and a wide range of relevant surface variations. Such measurements can therefore identify a lens made in accordance with the present invention very easy.

In an embodiment, the curvature results in a loss of light, within a circle with a diameter of 4 mm around said optical centre, of between about 2% to about 15%. In fact, usually the recessed part extends further than 4 mm in radial direction. In the calculations of the loss of light, reference is made to the blending parts which are enclosed by or are positions within two meridians or, to be more precise, semi-meridians running from the optical centre to the rim of a lens.

The actual loss of light, or better loss of intensity, can be measured with a PMTF system which is commercially available from Lambda-X SA Rue de l'industrie 37 1400 Nivelles Belgium. This instrument is capable of measure the loss of intensity. The procedure for this measurement will be discussed below in the description of embodiments.

In an embodiment, the main lens part has an optical power of between about −10 to about +30 dioptre.

In an embodiment, the recessed part is positioned at a distance of less than 1.5 mm from said optical centre. In this respect, the distance is defined as the nearest radial distance from the optical centre.

In an embodiment, the near part has a relative dioptre of about +1.50 dioptre to about +4.00 dioptre with respect to said main lens part. Thus, it allows use as a reading part, for instance. The optics of the central part as well as of the main lens part and of the recessed part can furthermore be designed to be toric, cylindrical or be designed to compensate higher order aberrations. These types of lens design are as such known to a skilled person, and can additionally be applied to the various lens parts of the current invention.

In an embodiment, the semi-meridian boundary or boundaries of said recessed lens part with said main lens part have a curvature resulting in a loss of light, within a circle with a diameter of 4 mm around said optical centre, of below about 10%. This very low loss of light, in particular in combination with the refraction away from the optical axis, already results in a higher contrast sensitivity and good reading ability.

In an embodiment, the main lens part has a curvature with substantially a curvature radius Rv, and the outer limit of the recess, i.e. its surface, lies on or within the curvature radius Rv.

In an embodiment, the ophthalmic lens further comprises a central part which has a relative optical power of −2.0 to +2.0 dioptre with respect to said main lens part. Thus, it may be possible to require a recessed part to be less deep and thus the blending parts to have less influence.

In an embodiment, the size of said central part is such that it fits within a circumscribing circle with a diameter of about 0.2-3.0 mm. Thus, it was found that distance vision would be influenced as little as possible by the recessed part. In an embodiment, the size of said central part is such that it fits within a circumscribing circle with a diameter of about 0.2-2.0 mm. In an embodiment, said central part is substantially circular.

In an embodiment of the lens with a central part, the lens comprises a further blending part between the central part and the recessed part. This blending part usually is concentric or almost concentric with respect to the optical axis. In an embodiment, the further blending part has a smooth transition. Alternatively, the slope has a kink. In this embodiment, the first derivative of the slope is discontinuous. Thus, the curvature radius of the surface has a kink. An advantage of this embodiment is that the recessed part will be less deep with respect to the main lens part. Alternatively, the further blending part is close to, approaches or is a step function. As this further blending part is concentric, this causes little disturbance in vision.

In an embodiment, the recessed part is bounded by semi meridians running though said optical centre, the recessed part thus having the shape of a meridian zone. In fact, the blending parts which blend the main lens part and the recessed part thus follow meridians as much as possible. In fact, such a blending part will be arranged between two semi meridians running through the optical centre.

In an embodiment comprising said central part, said recessed part is at at least one boundary bounded by said central part.

In an embodiment comprising said central part, said central part has a cross section of about 0.60-1.20 mm. This allows a recessed part which influences for instance contrast sensitivity as little as possible.

In an embodiment comprising said recessed part shaped as a meridian zone said recessed part has an included angle of about 160-200 degrees. In such an embodiment, at least two boundaries with the main lens part substantially follow meridians. In practice, these boundaries are formed by blending parts. As already stated above, usually such a blending parts is clamped between two semi meridians. In practice when using an optimised curve explained below, the blending part will not exactly follow a meridian, but will be slightly curved. In an embodiment said recessed part has an included angle of about 175-195 degrees.

In an embodiment, the ophthalmic lens has a cross section of about 5.5-7 mm. In particular in case of an intraocular lens, or another oculary supported lens like a contact lens, it will to in such a diameter range.

In an embodiment the main lens part is in the form of a distance lens.

In an embodiment the recessed part forms a reading part.

In an embodiment comprising said central part, said recessed part is bounded by two semi meridians and a line of latitude concentric and at a distance from said central part.

In an embodiment said recessed part comprises at least two sub-zone having optical powers which differ.

In an embodiment, these sub-zones are concentric.

In an embodiment optical powers of said sub-zones increase in radial direction. In an embodiment optical powers of said sub-zones decrease in radial direction In an embodiment the optical power of the recessed part increases in radial direction. Thus, it is possible to provide an intermediate vision part between the main lens part and, if present, central part, and a near or reading part provided in the recessed part. The blending between these increasing optical power regions or zones should be designed carefully. It may require compensation of less step height in blending parts.

In an embodiment said recessed part comprises a diffractive optics part. The diffractive optics may be superposed unto the surface of the recessed part. In general, a diffractive optical superposed part on a lens surface is known. In case of a recessed part, however, it may allow the recessed part to be less deep.

In an embodiment, the recessed part comprises a first, central subzone and two further subzones circumferentially neighbouring at both sides of said first subzone. In an embodiment thereof, said first subzone has an optical power larger than the optical power of the further subzones. In an embodiment, the two further subzones have an optical power larger than the optical power of said remaining lens part.

In an embodiment meridians bound said recessed part. In fact, two semi-meridians bound said recessed part, thus defining the recessed part as a sector part or wedge part (like a wedge of pie). If the ophthalmic lens has a central part as defined above, this sector part has a part from the forming a sector part having a part of the tip taken away.

In an embodiment, the blending parts are within meridian which enclose an angle of less than 17°, in a particular embodiment less than 15°. In an embodiment, blending parts can even be designed to be within meridian which enclose an angle of less than 5°. This, however, requires a very careful design of the curves and slopes or derivatives of the curves.

In an embodiment said the slope of the blending parts has an S-curve and have a steepness with a slope or first derivative at a central range of the blending part at 1.6 mm from said optical centre of more than 0.1, in an embodiment more than 0.4 at its steepest part. In an embodiment said blending parts have a steepness with a slope or derivative at a central range of the blending part at 2.8 mm from said optical centre of more than 0.2, in an embodiment more than 0.7 at its steepest part.

In an embodiment, at least one of said blending parts, in particular at least one semi meridian blending part, has an S-shaped curve which follows a first parabolic curve running from the main lens part surface towards the surface of the recessed part, having an intermediate curve part connecting to said first parabolic curve, and continuing with following a second parabolic curve ending at the recessed surface.

In an embodiment, said intermediate curve part at its steepest part has a first derivative of at least 0.05 at 0.4 mm from said optical centre, in an embodiment at least 0.1 at 0.8 mm, in an embodiment at least 0.15 at 1.2 mm, in an embodiment at least 0.2 at 1.6 mm, in an embodiment at least 0.3 at 2.0 mm, in an embodiment at least 0.4 at 2.4 mm, in an embodiment at least 0.5 at 2.8 mm.

The invention further pertains to an add-on intraocular lens to be inserted in the bag, the sulcus, as cornea inlay or an anterior chamber lens, comprising the ophthalmic lens according to any one of the preceding claims, wherein said main lens part has an optical power of about −10 to +5 dioptre.

The invention further relates to an ophthalmic lens comprising a main lens part having substantially a curvature radius Rv, a substantially circular central part having a first optical property and having a cross section of about 0.2-2.0 mm, and a meridian part comprising a recess which is bounded by said substantial circular central part, by two meridians running through the centre of said circular part, and by a lower boundary which is substantially concentric with respect to said circular part, said meridian part formed as a recess in said lens, the outer limit of the recess lying on or within the curvature radius Rv, said meridian part comprising a reading part.

The invention further relates to a method for the production of one of the ophthalmic lenses described above, comprising a step of turning, in which a lens blank is positioned on a rotating machining holder and is subjected to the influence of one or more material-removing devices, characterized in that during the turning step the rotating lens and said material-removing device are moved to and away from one another in the direction of the axis of rotation, in order to form at least one recessed portion in said ophthalmic lens. This production method allows production of lenses having the properties required.

The invention further relates to an ocularly supported multifocal corrective lens provided with a substantially circular central lens portion, a lower lens portion in a lower lens part neighbouring said central lens portion, and a further lens portion, the lower lens portion comprises a recess comprising two sides which run from said central lens portion towards the rim of the lens, the outer limit of the lower lens portion lies on or within an imaginary sphere having its origin and radius of curvature coinciding with the radius Rv of said further lens portion, wherein said two sides provide sloping from the further lens portion surface to the recessed surface of the lower lens portion, said sloping following a first parabolic curve running from the further lens portion surface towards the lower lens portion surface, and continuing with following a second parabolic curve ending at the recessed surface.

The invention further relates to an ophthalmic lens comprising a main lens part, a recessed part, an optical centre, and an optical axis substantially through said optical centre, said main lens part having at least one boundary with said recessed part, said recessed part positioned at a distance from said optical centre, boundaries of said recessed lens part with said main lens part are formed as blending parts which are shaped to refract light away from said optical axis, said main lens part, central part, recessed part and blending parts mutually positioned and shaped for providing a LogCS characteristic under photopic light conditions, usually at about 85 cd/m$^2$, within 6 months post operative, in a spacial frequency (cpd) between 3-18 which is at least between the population norm of 11-19 years and 50-75 years.

In an embodiment of this lens, in a spacial frequency (cpd) between about 6 and 18, its LogCS characteristic under photopic light conditions, within 6 months post operative, usually at about 85 cd/m$^2$, is in the range of normality above the population norm of 20-55 years old adults with healty eyes.

The invention further relates to an intraocular lens comprising a main lens part, a recessed part positioned at a distance from an optical centre, and a central part in said optical centre and which is substantially circular, has a diameter of about 0.8 to 2.8 mm, and at one side bounding said recessed part, wherein the diameter of said central part is adapted to the pupil diameter of the wearer.

In an embodiment, the diameter of said central part is about 20-40% of the pupil diameter of the wearer at office lighting conditions, i.e. 200-400 lux. Thus, the IOL can be custom-made.

Various aspects and/or features described in this text may be combined. Features and aspects may also form part of one or more divisional applications referring, for instance, to aspects of the production resulting in methods, specific types of ophthalmic lenses, like the once mentioned in this text, or to specific features like the blending or transition zones, the recessed part and its features, or the central part.

DESCRIPTION OF EMBODIMENTS WITH REFERENCE TO THE DRAWINGS

Figure 2:
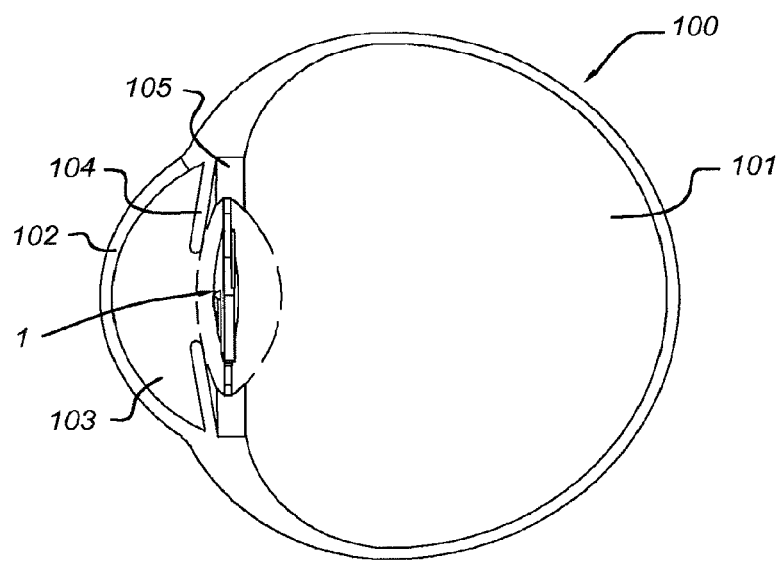
Figure 7:
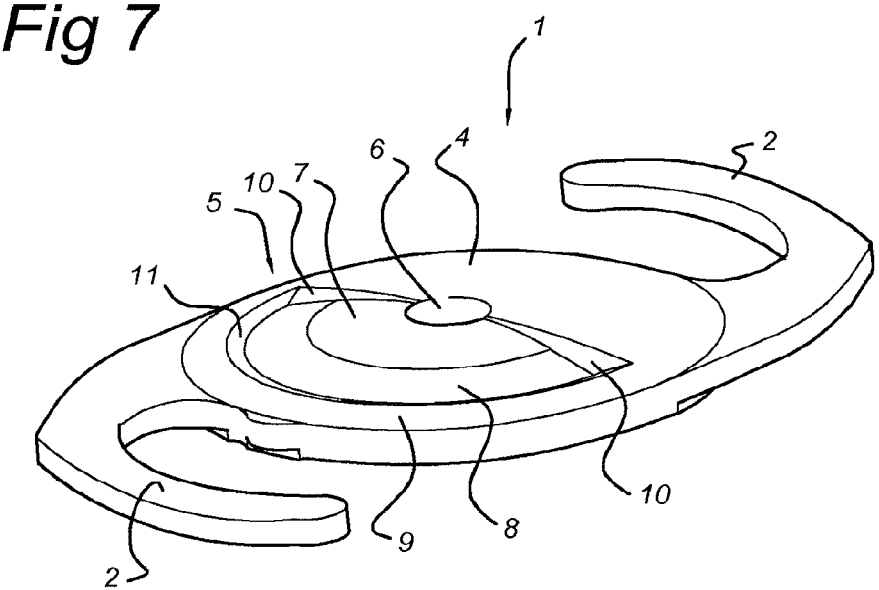
Figure 8:
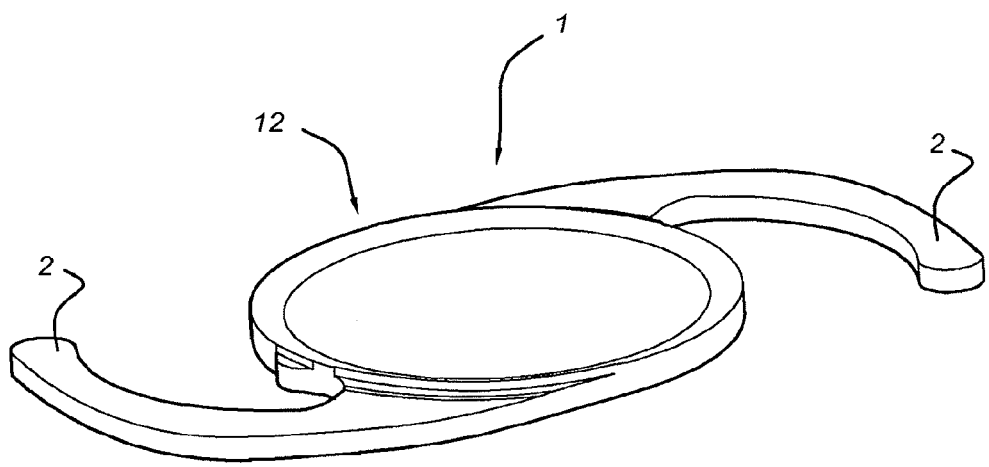
Figure 9:
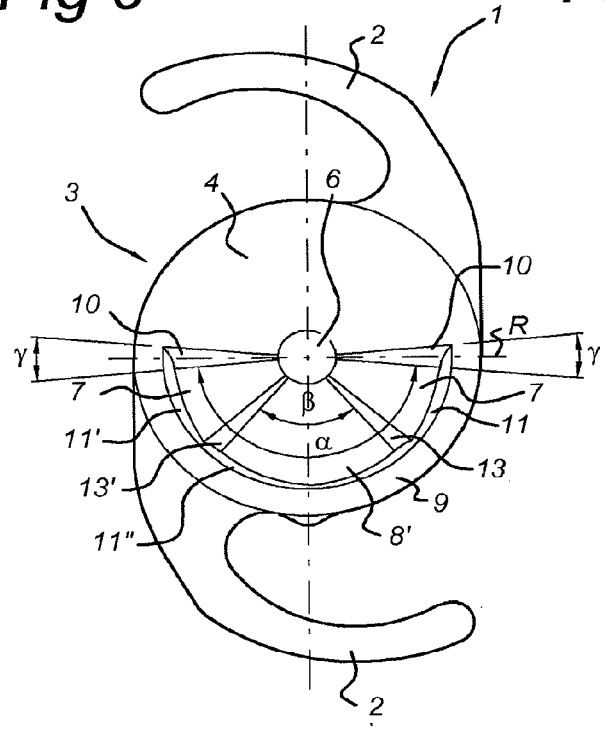
Figure 10:
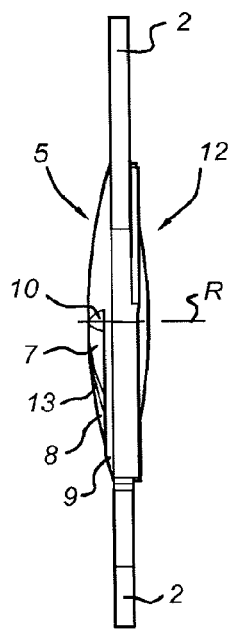
Figure 11:
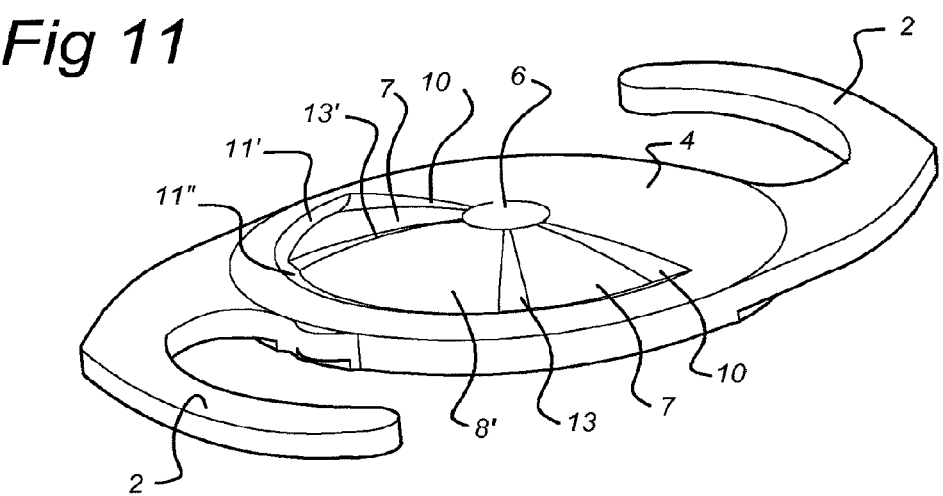
Figure 15:
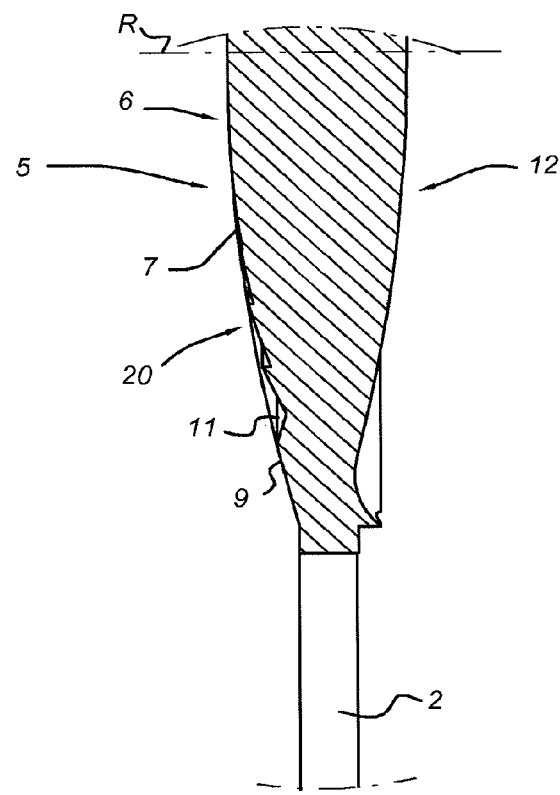
Figure 16:
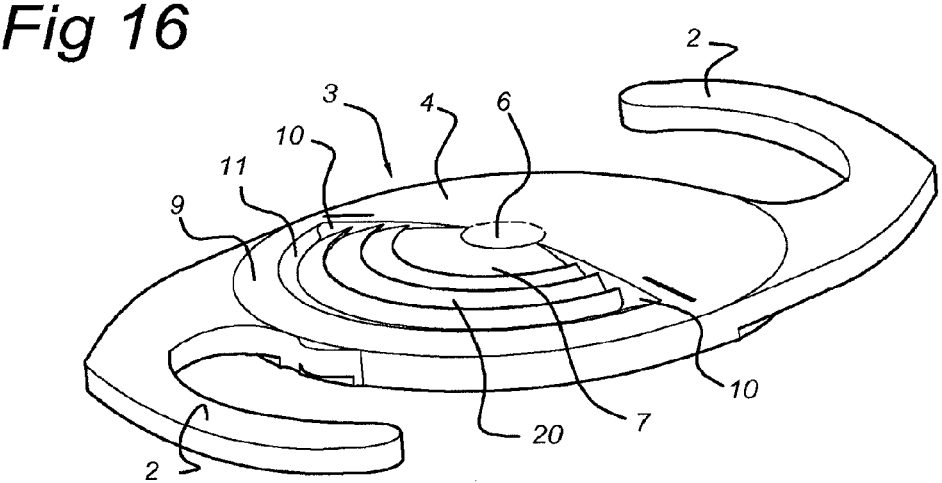
Figure 17:
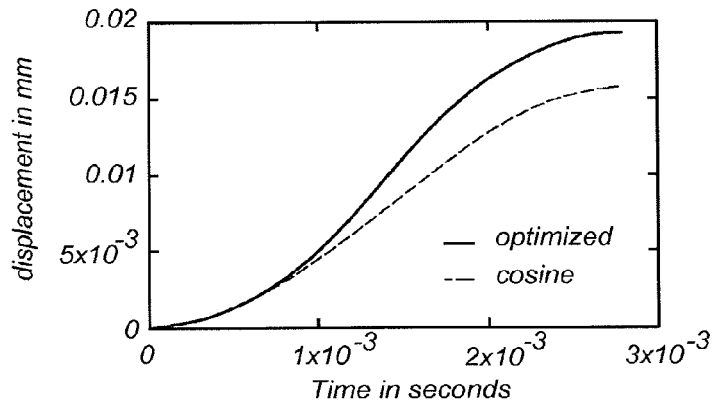
Figure 18:
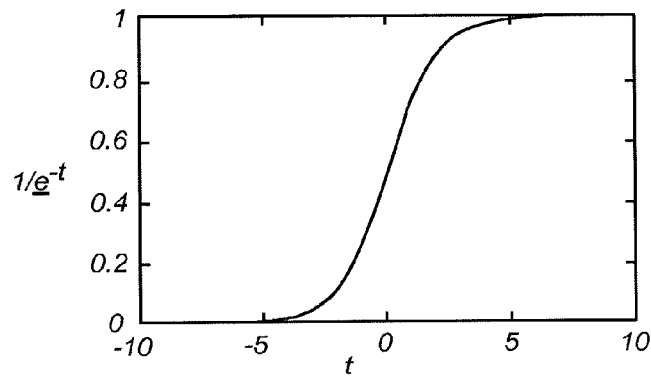
Figure 19:
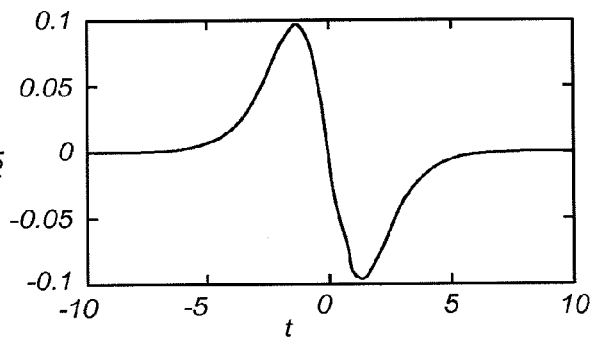
Figure 20:
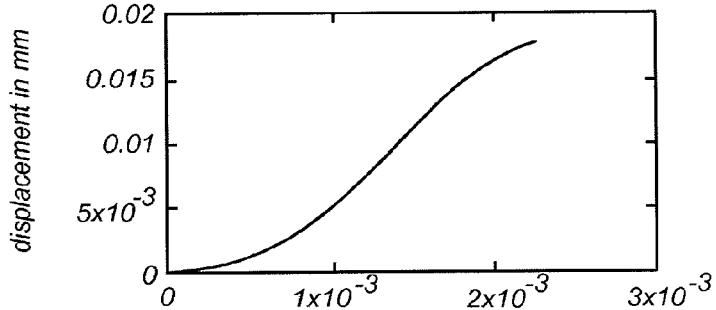
Figure 21:
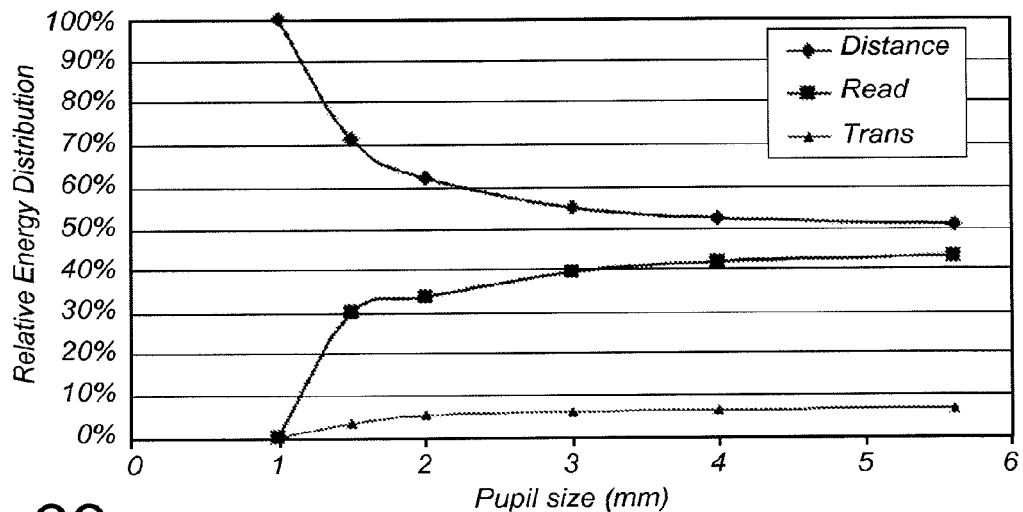
Figure 27:
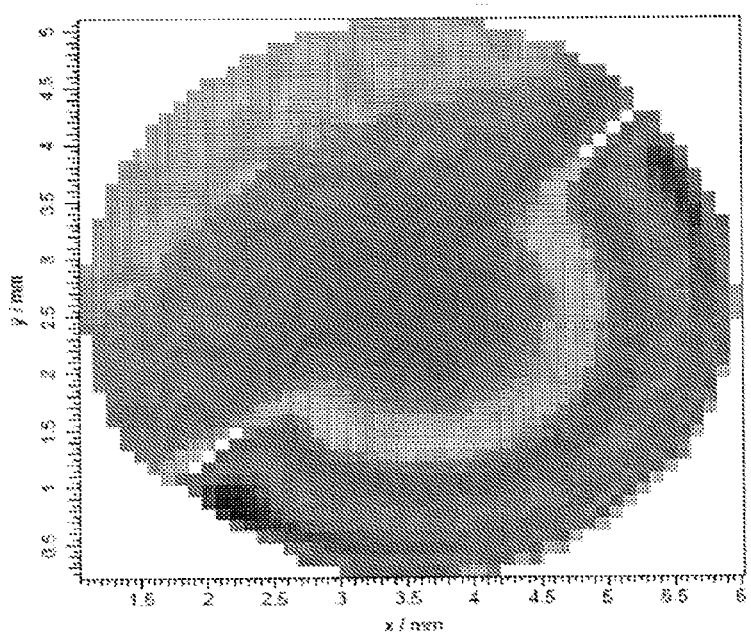
Figure 28:
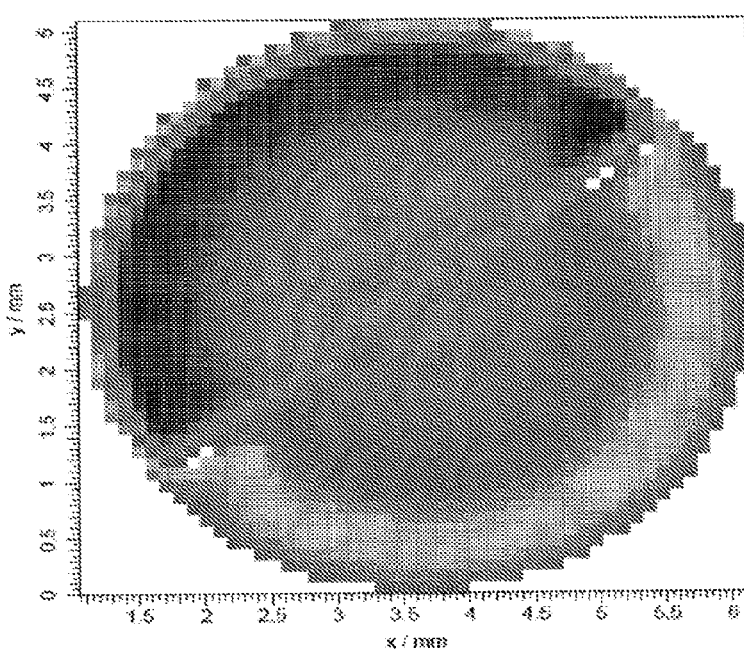
Figure 29:
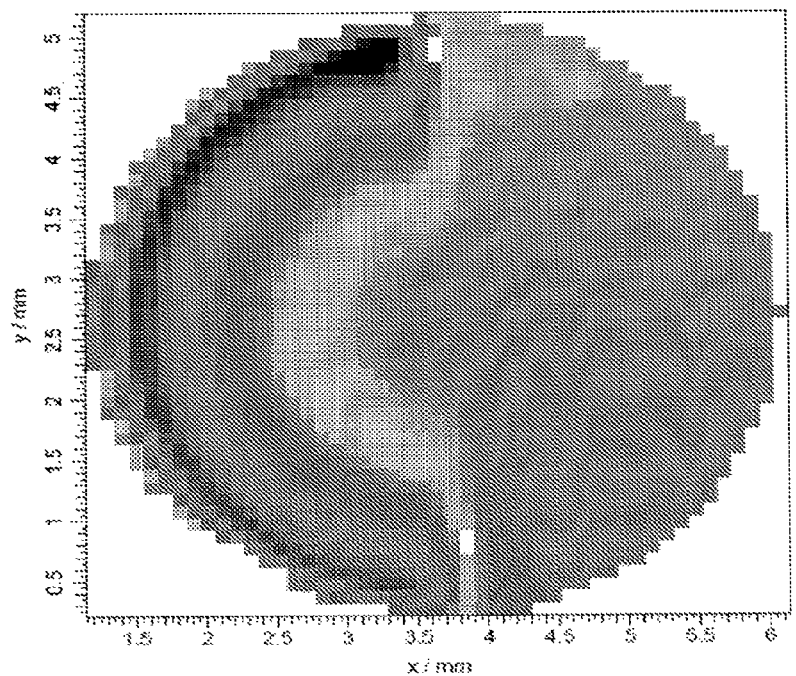
Figure 30:
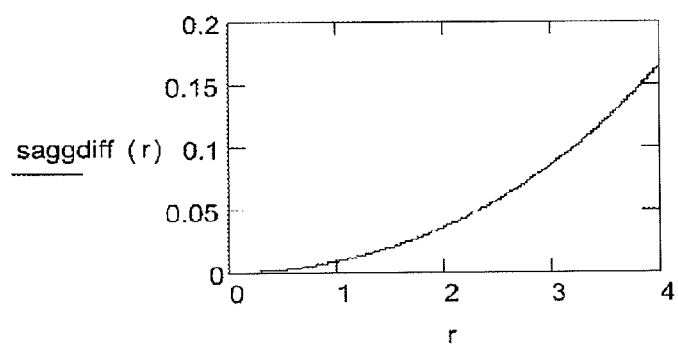
Figure 31:
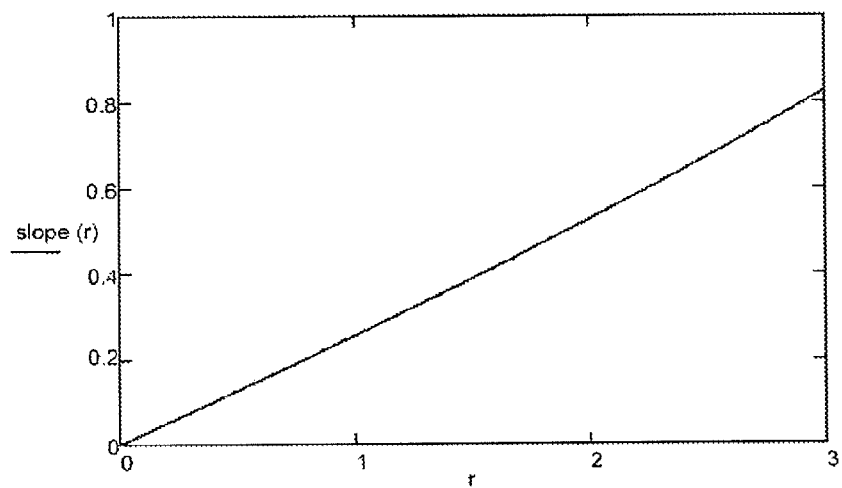
Figure 32:
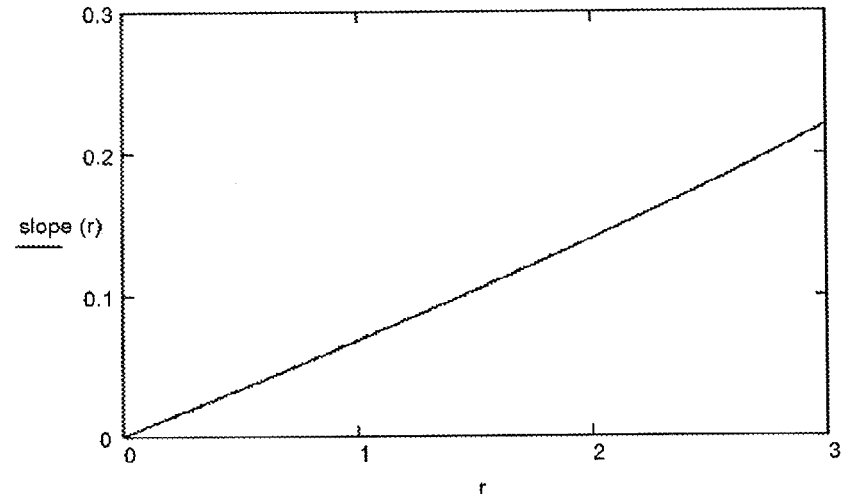
Figure 33:
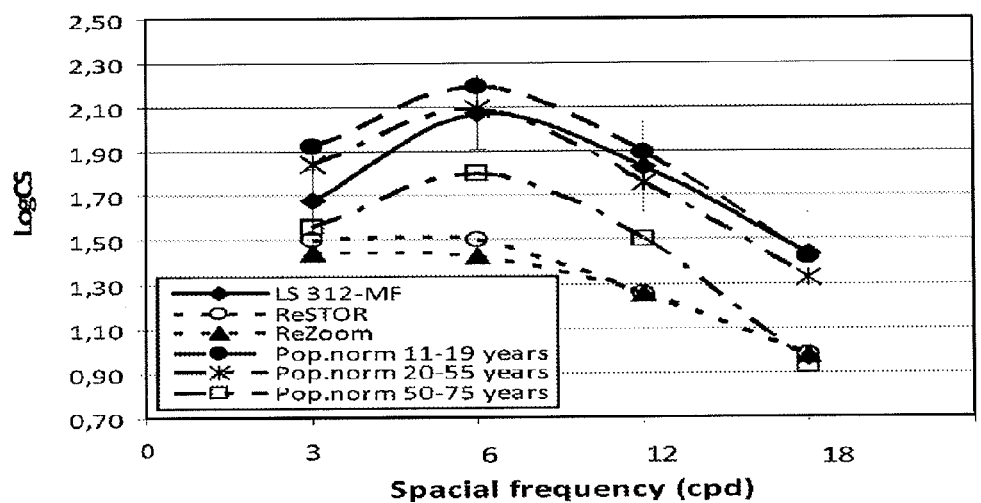
Figure 34:
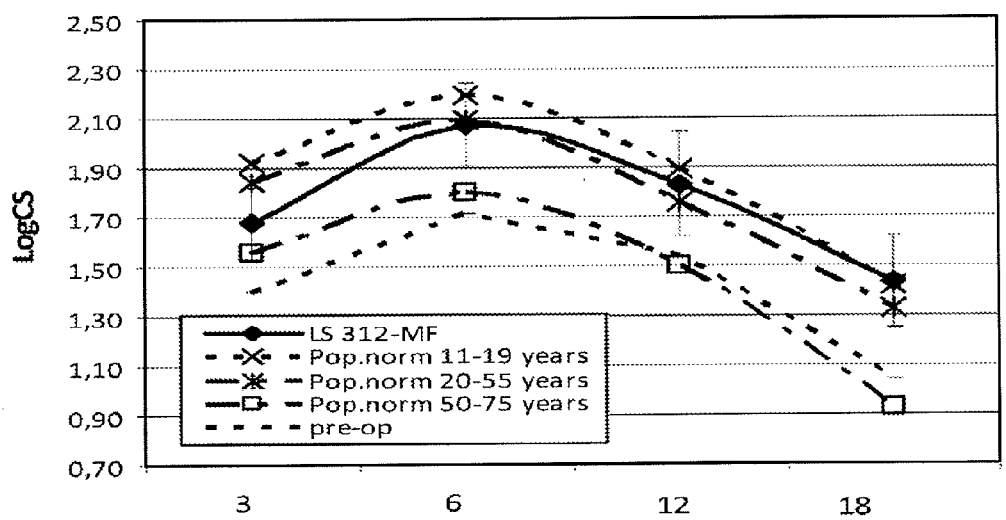
Figure 35:
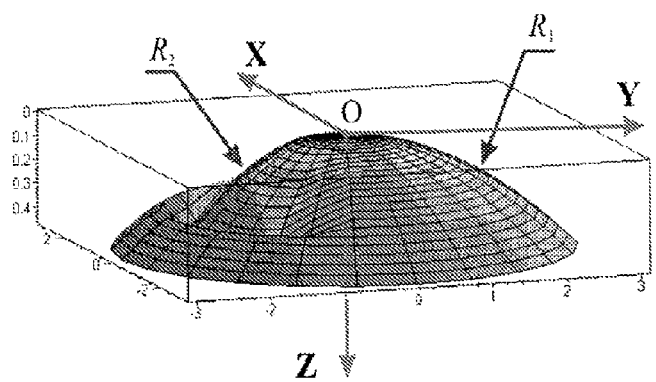
Figure 36:
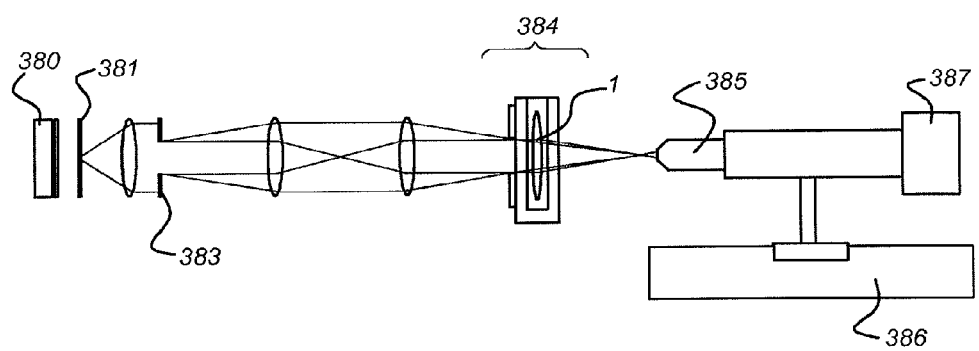

The invention will be further elucidated referring to embodiments of a Multifocal Sector Ophthalmic Lens, (MSOL) shown in the attached drawings, showing in:

FIG. 1 a cross section of a human eye;

FIG. 2 a cross section of a human eye with an IOL;

FIG. 3 a front view of an embodiment of an MSIOL with an optical central part and a recessed part;

FIG. 4 a side view of the MSIOL according to FIG. 3;

FIG. 5 a cross sectional view over line IV of the MSIOL according to FIG. 3;

FIG. 6 a detail of the cross section according to FIG. 5;

FIG. 7 a perspective front side view of the MSIOL according to FIG. 3;

FIG. 8 a perspective back side view of the MSIOL according to FIG. 3;

FIG. 9 a front view of another embodiment of an MSIOL with a recessed part subdivided in three meridianally divided optical sectors and one central optical sector;

FIG. 10 a side view of the MSIOL according to FIG. 9;

FIG. 11 a perspective front side view of the MSIOL according to FIG. 9;

FIG. 12 a front view of a further variant of the MSIOL with a recessed diffractive semi-meridian sector element;

FIG. 13 a side view of the MSIOL according to FIG. 12;

FIG. 14 a cross sectional view over line XIV of the MSIOL according to FIG. 12;

FIG. 15 a detail of the cross section according to FIG. 14;

FIG. 16 a perspective front side view of the MSIOL according to FIG. 12;

FIG. 17 a comparison between a optimised transition trajectory and cosine trajectory of a transition or blend zone or part, illustrating that in the same time with the optimised profile a larger displacement is possible;

FIG. 18 the sigmoid function without any scaling and translation on the interval [−10,10];

FIG. 19 the experienced or effective acceleration (second derivative) during the sigmoid transition;

FIG. 20 the reduction of the transition zone width by calculating the needed transition time and distance according the method described in this document locally, the transition zone width is zero near the centre;

FIGS. 21-26 graphs showing the energy distribution in various parts of several embodiments of ophthalmic lenses;

FIGS. 27-29 measured data of ophthalmic lenses;

FIGS. 30-32 graphs of steepness's of blending or transition zones or parts;

FIGS. 33 and 34 test results showing the LogCS against the spatial frequency;

FIG. 35 showing a surface model of one of the embodiments;

FIG. 36 a schematic setup of measuring instrument PMTF.

DETAILED DESCRIPTION OF EMBODIMENTS

A preferred embodiment of the invention is now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Unless defined otherwise, all technical and scientific terms used herein have the same meanings as commonly understood by one of ordinary skilled in the art to which this invention belongs. Generally, the nomenclature used herein and the laboratory procedures are well known and commonly employed in the art. Conventional methods are used for these procedures, such as those provided in the art and various general references.

It should be understood that the anterior optical sectors are preferably concentric with the geometric centre of the posterior surface A "vertical meridian" refers to an imaginary line running vertically from the top, through the centre, to the bottom of the anterior surface of an MSIOL when said MSIOL is maintained at a predetermined orientation into the eye A "horizontal meridian" refers to an imaginary line running horizontally from the left side, through the centre, to the right side of the anterior surface of an MSIOL when said MSIOL is maintained at a predetermined orientation into the eye. The horizontal and vertical meridians are perpendicular to each other.

"Surface patches" refer to combinations of curvatures and lines that are continuous in first derivative, preferably in second derivative, from each other.

A "outer boundary", in reference to a zone other than a central optical zone on the surface of an MSIOL, refers to one of two peripheral boundaries of that zone which is further away from the geometric centre of the anterior surface.

An "inner boundary", in reference to a zone other than a central optical zone on the surface of an MSIOL, refers to one of two peripheral boundaries of that zone which is closer to the geometric centre of the anterior surface.

A "semi-meridian" refers to an imaginary line running radially from the geometric centre of the anterior surface of an MSIOL to the edge of the lens.

The "upper portion of the vertical meridian" refers to one half vertical meridian that is above the geometric centre of the anterior surface of an MSIOL, when said lens is maintained at a predetermined orientation inside an eye.

The "lower portion of the vertical meridian" refers to one half vertical meridian that is below the geometric centre of the anterior surface of an MSIOL, when said lens is maintained at a predetermined orientation inside an eye.

A "continuous transition", in reference to two or more sector, means that the slope of these sectors are continuous at least in first derivative, preferably in second derivative.

A "vertical meridian plane" refers to a plane that cuts through the optical axis of an MSIOL and a vertical meridian on the anterior surface of the MSIOL.

As used herein in reference to the sectors or parts of an MSIOL the terms "Baseline Power", "optical power", "Add Power" and "Dioptre power" refer to the effective optical or Dioptre power of a sector when the lens is part of an ocular lens system such as for instance a cornea, a MSIOL, a retina and the material surrounding these components. This definition may include the effects of the divergence or angle of light rays intersecting the MSIOL surface caused by power of the cornea. In certain instances, an algorithm for calculating the Dioptre power may begin with a ray-tracing model of the human eye incorporating a subdivided sector MSIOL. At a particular radial location on the MSIOL surface Snell's law may be applied to calculate the angle of the light ray following the refraction. The optical path length of the distance between a point on the surface and the optical axis (axis of symmetry) may be used to define the local radius of curvature of the local wave front. Using such an approach, the Dioptre power is equal to the difference in indices of refraction divide by this local radius of curvature.

The present invention aims to improve ophthalmic lenses, and in one aspect relates to an novel Multifocal Sector Intra Ocular Lens (MSIOL) with at least two semi-meridian optical sectors where at least one of the semi-meridian optical sectors is radial or angular subdivided and could comprise an inner sector, an intermediate sector, and an outer sector, located within the (imaginary) boundary of the distance part. The inner sector has a first optical power, the intermediate sector adjacent to the first optical power has a second optical power. The outer sector adjacent to the second optical power has a third optical power whereas the step height between the boundaries of the semi-meridian sectors are joint by means of a optimised transition profile to maximize light energy directed to the macula and to reduce blur and halo's at bigger pupil size. The ophthalmic lens semi-meridian sectors could have a continuous power profile or the discrete optical sub circle sectors blend together or combinations thereof. The subdivided sector(s) will provide a clear vision at reading and intermediate distances. Whereas the distance vision and contrast sensitivity remain comparable with an mono focal ophthalmic lens with reduced blur and halo's at bigger pupil size. The present invention may also be configured to perform well across eyes with different corneal aberrations (e.g., different asphericities), including the spherical aberration, over a range of decentration.

The ophthalmic lens may be designed to have a nominal optical power for distance vision, defined as "Baseline Power", usually of the main lens part, an "Add power" added on top of the nominal optical power or Baseline power, and intended for the reading vision. Often, also an intermediate optical power is defined suited for the particular environment in which it is to be used. In case of an MSIOL, is anticipated that the nominal optical power or baseline power of an MSIOL will generally within a range of about −20 Dioptre to at least about +35 Dioptre. The "Add power" will generally be in a range of about +1 Dioptres to at least about +5 Dioptre. Desirably, the nominal optical power of the MSIOL is between about 10 Dioptres to at least about 30 Dioptre, the "Add power" will be between about +1.50 and +4.00 Dioptre. In certain applications, the nominal optical power of the MSIOL is approximately +20 Dioptre, and the Add power about +3.00 Dioptre, which is a typical optical power necessary to replace the natural crystalline lens in a human eye.

In FIG. 1, a schematic view of a human eye 100 with its natural lens 106 is shown. The eye has a vitreous body 101 and cornea 102. The eye has an anterior chamber 103, iris 104 and ciliary muscle 105 which hold the lens. The eye has a posterior chamber 107. In FIG. 2, the eye 100 is shown with an intra ocular lens 1 replacing the original lens 106.

In FIG. 3, an embodiment of an intra ocular lens (IOL) 1 is shown which has haptics 2 and a lens zone or lens part 3. The lens part 3 is the actual optically active part of the IOL 1. The haptics 2 can have a different shape. In this embodiment, lens part 3 has a central part 6 which is usually substantially circular. It may deviate a little from an absolute circle, but in most embodiments it is as round or circular as possible in the specific further lens design. The lens part 3 further has a meridian part in a recess area. This recess is below the surface of the curved surface of the remaining lens part 4 of lens part 3. In other words, the curved surface of the remaining lens part 4 has a radius of curvature Rv, and the recess of the meridian part lies on or within the curvature radius Rv (see FIG. 4). It should be clear that curved surface of the lens part can be non-spherical or aspheric. In fact, the curved surface can be as described in for instance U.S. Pat. No. 7,004,585 in columns 6, 7 and 8. In particular the Zernike polynomials can be used to describe any curved surface of an ophthalmic lens.

In this embodiment, the meridian part is divided into two concentric sub-zones 7 and 8.

The various parts, i.e. the central part 6, inner meridian part 7 And outer meridian part 8, each have a have an angle of refraction or power which differs from the remaining lens part 4. When the lens part 3 is considered as part of a sphere having an axis through the crossing of lines R and S, then the central part 6 can also be defined as bounded by a first line of latitude. In this definition, sub-zone 7 can be defined as bounded by two meridians, the first line of latitude and a second line of latitude. Following this same definition, sub-zone 8 can be defined as bounded by the two meridians, the second line of latitude and a third line of latitude. In most embodiments, the meridian part (in cartography an area of this shape is also referred to as "longitudinal zone") is referred to as a "reading part".

The MSIOL comprises a near part or reading part which is bounded on or within the lens zone 3 whereas the transition between those parts is performed with a cosine function or sigmoid function, but desirably joined with the optimized transition function discussed below. In general terms, these general transitions curves are referred to as S-shaped curves. These transitions have a width and are referred to as blending zone or transition zone.

The near or reading part in an embodiment has an included angle $\alpha$ between about 160 and 200 degrees. In a further embodiment, the included angle is between about 175 and 195 degrees. The reading part can optically be sub divided into at least two imaginary circle sectors 7 and 8, forming a continuous transition surface radial about the optical axis or geometric axis. The required shape (and curvature of the recessed surface) of those circle sectors 7, 8 can be calculated using ray tracing to control at least the amount of spherical aberration and further to avoid image jumps. The reference lines in the lens part 3 are imaginary and for dimensional reference purpose. They are, however, not visible in the real product.

The lens part 3 in this embodiment has an outer diameter between about 5.5 and about 7 mm. In a preferred embodiment, it is about 5.8-6.2 mm. The central part or inner sector 6 has a optical power at least equal to the baseline power. Desirably, the optical power of the inner circle sector or central part 6 is between 0% and 100% of the Add power.

The central part 6 in an embodiment has a diameter of between about 0.2 mm and 2.0 mm. In an embodiment, the diameter of the central part 6 is between about 0.60 and 1.20 mm. In case the central part 6 is not absolutely round, it is a circumscribing circle having the diameter range mentioned here.

Circle Sector or central part 6 has a optical power at least equal to the baseline power. In this embodiment, the recessed part has two indicated subzones, a first subzone 7 near the central part 6. This inner subzone has a latitude radius of between about 1.5 and 2.3 mm. In an embodiment, it is between about 1.8 and 2.1 mm. The outer subzone 8 has an optical power equal or greater than the baseline power. In an embodiment, the optical power is between 0 and 100% of the Add power. Thus, it forms an intermediate between the main lens part or the central part, and a near part in outer subzone 8. The latitude radius of outer subzone 8 has a dimension between about 2.2 and 2.7 mm. In an embodiment, it can be between about 2.3 and 2.6 mm. In this embodiment, the main lens part almost continues at part 9. The outer limit radius where the lens main lens part 4 continues can have a latitude radius of between about 2.6 and 2.8 mm. In an alternative embodiment, several concentric subzones can be provided in order for the recessed part to disturb or influence the central part for distance vision as little as possible.

The IOL 1 has two semi meridian blending zones or blending parts 10 bounding the recessed part 7, 8. These semi meridians bounding blending parts 10 have an angle $\gamma$. In an embodiment, the angle will be less than 35°. In an embodiment, it will be less than 17°. In particular, the angle $\gamma$ will be less than 5°. Usually, it will be more than about 1°.

The recessed part in this embodiment further has a blending zone 11 which is concentric with respect to the optical axis R. Main lens part 4 continues in the concentric region indicated with reference number 9.

In FIGS. 9-11, several view of another example of an ophthalmic lens is shown, as an Intra ocular lens. In this embodiment, again the recessed part is divided into subzones. Here, the two outer subzones 7 are angularly arranged at both sides of a central subzone 8'. The MSIOL comprises a main lens part 4 with a recessed part with a total included angle $\alpha$ between 160 and 200 degrees, desirably between 175 and 195 degrees. The included angle of the outer subzones 7 is between about 10 and 30 degrees. In an embodiment, it is between about 15 and 25 degrees. The included angle $\beta$ of the central subzone 8' is between about 80 and 120 degrees. In an embodiment, the central subzone 8' is between 85 and 100 degrees.

The total included angle of the subzones 7, 8' for near and intermediate vision are bounded by the main lens part 4. The transitions or blend zones between the various parts follow a cosine function or sigmoid function. In an embodiment, they follow an optimized transition function described below. Due to this optimized transition profile at least one of those imaginary transition lines will be curved.

The subzones 7 and 8' are radial arranged around the geometric axis. The optical shape of those circle parts are ray traced to control the amount of spherical aberration and further to avoid image jumps. The reference lines in the lens parts are imaginary and for dimensional reference purpose only and are not visible in the real product. The lens part has a outer diameter dimension between 5.5 and 7 mm. In an embodiment, the diameter is about 6 mm. The central part 6 has a optical power at least equal to the baseline power of the main lens part. The diameter of central part has a diameter of between about 0.2 mm and 2.0 mm. In an embodiment, the diameter is between about 0.40 and 1.20 mm. The recessed part can have a radial width of between about 1.5 and 2.3 mm. In an embodiment, the width is between about 1.8 and 2.1 mm. In an embodiment, the outer subzones 7 have a optical power of about 30 to 60% of the Add power, i.e. about 30-60% of the relative dioptre of the central part 8'.

The MSIOL as shown in FIGS. 3-8 may also be used in conjunction with another optical device such as a Diffractive Optical Element (DOE) 20. In an embodiment shown in FIGS. 12-16, such an embodiment is shown. That MSIOL comprises a recessed lens part 7 shaped as a refractive semi-meridian part having a first optical power. The total included angle $\gamma$ of the recessed part can be between about 160-200 degrees. In an embodiment, the enclosed angle is between about 175-195 degrees. The diffractive optical element 20 is superposed on the surface of the recessed part 7. It is shown in an exaggerated way with larger scaled features. In practice, the features of the diffractive optical element 20 can be around about 0.5-2 micron in size. In an embodiment, the diffractive optical element 20 can be provided in the outer radial part of the recessed part 7. Thus, the central part 6 can have the same optical power or differ only up to about 1 dioptre with respect to the main lens part 4. The first subzone of the recessed part 7 can differ 0.5-2 dioptre with respect to the central part 6.

The refractive reading part as described in FIGS. 3-8 may have an additional DOE element to correct for chromatic aberration or to further improve the distance and reading performance of the MSIOL. This is depicted in FIGS. 12-16. The DOE part 20 may be ray traced to control the amount of spherical aberration and further to reduce halo's and glare. The lens zone 3 also has a outer diameter of between about 5.5 to 7 mm. In an embodiment, it is about 5.8-6.2 mm. The central part 6 has a optical power at least equal to the baseline optical power of remaining lens part 4. Desirably, the optical power of the inner circle sector 7 is between 0% and 100% of the Add power. The embedded semi-meridian circle sector used as the refractive base for the DOE 20 has a optical power 10% and 100% of the Add power. The recessed part has a width (from the end of the central zone to blending past 11) between 1.5 and 2.3 mm. In an embodiment, it is between 1.8 and 2.1 mm. The DOE 20 may be configured for the baseline power and the intermediate Add power.

In an embodiment, transition zones or blend zones 10 bounding the recessed part of the embodiments described in FIGS. 3-16 can follow a cosine function or a sigmoid function. In an embodiment, the transition zones 10 follow an optimized transition function described below. The transition or blending zones 13 and 13' can also follow such a function.

EXAMPLES

Several lens configurations based on FIGS. 3-8 are presented below, for an IOL. For several pupil diameters, the area covered in $mm^2$ by the various sectors (zones or regions) are shown. In several graphs, the theoretically determined, relative light energy based on the area covered by the various sectors is shown. (Sector Radius Central refers to the radius of the central part). These theoretical example calculation were done as if the lens has no radius of curvature, i.e. a flat surface. This method has been chosen to simplify the calculation because the curvature of the lens surface will change with the optical power. The equations for calculating the surface area of a transition area used in the embodiments below are as follows.

$$A_{Pupil} = \frac{\pi}{4} D_{pupil}^2$$

$$A_{Near} = \frac{\alpha_{near} \cdot \pi}{360 \cdot 4} (D_{pupil}^2 - D_{dist}^2)$$

$$A_{Dist} = \frac{\alpha_{far} \cdot \pi}{360 \cdot 4} (D_{pupil}^2 - D_{dist}^2) + \frac{\pi}{4} D_{dist}^2$$

$$A_{Transition} = \frac{\alpha_{trans} \cdot \pi}{360 \cdot 4} (D_{pupil}^2 - D_{dist}^2)$$

It was found that these values can also be determined using measurements. To that end, an instrument called PMTF can be used. This instrument is available from Lambda-X SA, Rue de l'industrie 37, 1400 Nivelles, BELGIUM. In the measurement procedure, an IOL is placed in an ISO model eye. A schematic drawing of the principle of PMFT is shown in FIG. 36, showing a light source 380, a target 381 for providing a spacially defined light area, a collimating lens 382, an aperture 383, a set of lenses L1 and L2, An ISO eye model 384 holding the IOL in a cuvette, a microscope 385 on a translation table 386 and a CCD camera 387 mounted on said microscope 385. In the measurements used below, the eye model has a 4 mm diameter aperture for simulating the pupil.

The measurement procedure and data handling were as follow. The order of measurements of the IOLs can be reversed. In the measurements, an IOL with only one optical zone is measured, and the same IOL but with an optical zone according to the invention is measured using the same procedure.

The measurements are performed according to the normal use of the PMFT. In this case, first a reference IOL without recessed part was measured. In the focal plane the light within an image of the aperture was measured by integrating the calibrated intensity on the CCD sensor. Next, an IOL with recessed part was measured. To that end, first the different focal planes of the IOL and the focal plane of the reference IOL are located. The intensity was measured in the focal planes of the IOLs. Thus, in case of an IOL with a far region (the main lens part) and a near region in the recessed part, the light in two focal planes was measured. From the light measurements on the CCD camera, the light in the focal planes was added and compared to the light in the focal plane of the reference IOL. The measured values for light loss corresponded very well with theoretically calculated light loss.

Figure 24:
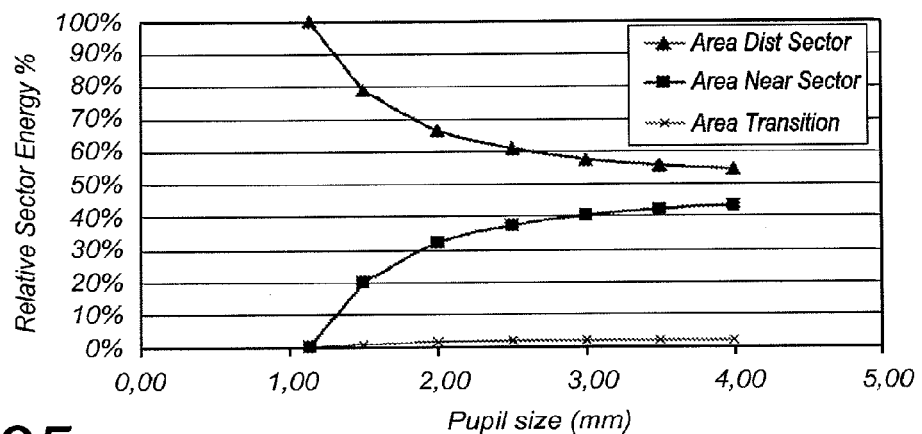

Embodiment 1, FIG. 24

| | | | | | | | | | | | | | | | |
|---|---|---|---|---|---|---|---|---|---|---|---|---|---|---|---|
| Sector Angle Distance | 182 | | | | | | | | | | | | | | |
| Sector Angle Near | 170 | | | | | | | | | | | | | | |
| Sector Angle Transitions | 8 | | each recess 4 degrees transition | | | | | | | | | | | | |
| Sector Radius Central | 0.57 | | | | | | | | | | | | | | |
| Pupil diameter | 4.00 | 4.00 | 3.50 | 3.50 | 3.00 | 3.00 | 2.50 | 2.50 | 2.00 | 2.00 | 1.50 | 1.50 | 1.14 | 1.14 |
| Area Pupil | 12.57 | | 9.62 | | 7.07 | | 4.91 | | 3.14 | | 1.77 | | 1.02 | |
| Area near sector | 5.45 | 43% | 4.06 | 42% | 2.86 | 40% | 1.84 | 37% | 1.00 | 32% | 0.35 | 20% | 0.00 | 0% |
| Area dist sector | 6.86 | 55% | 5.37 | 56% | 4.08 | 58% | 2.99 | 61% | 2.09 | 67% | 1.40 | 79% | 1.02 | 100% |
| Area transition | 0.26 | 2.0% | 0.19 | 2.0% | 0.13 | 1.9% | 0.09 | 1.8% | 0.05 | 1.5% | 0.02 | 0.9% | 0.00 | 0% |

Figure 25:
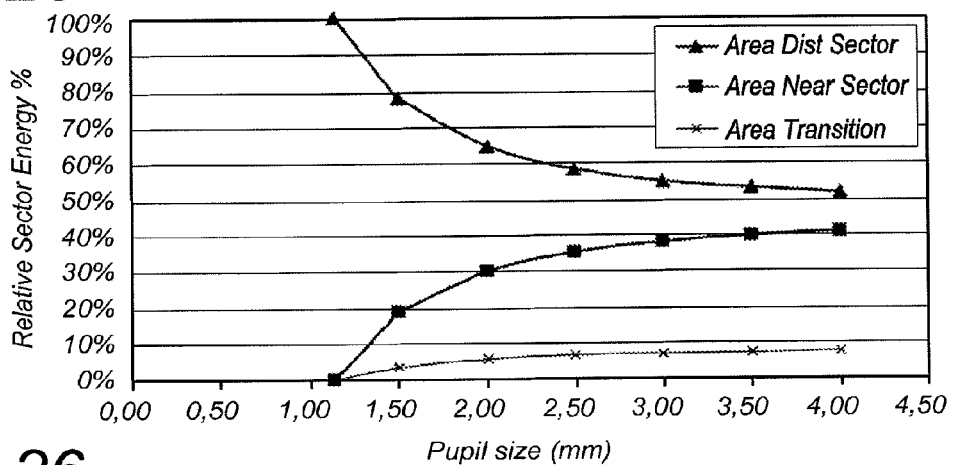

Embodiment 2, FIG. 25

| | | | | | | | | | | | | | | |
|---|---|---|---|---|---|---|---|---|---|---|---|---|---|---|
| Sector Angle Distance | | | | 170 | | | | | | | | | | |
| Sector Angle Near | | | | 160 | | | | | | | | | | |
| Sector Angle Transitions | | | | 30 | | each recess 15 degrees transition | | | | | | | | |
| Sector Radius Central | | | | 0.57 | | | | | | | | | | |
| Pupil diameter | 4.00 | 4.00 | 3.50 | 3.50 | 3.00 | 3.00 | 2.50 | 2.50 | 2.00 | 2.00 | 1.50 | 1.50 | 1.14 | 1.14 |
| Area Pupil | 12.57 | | 9.62 | | 7.07 | | 4.91 | | 3.14 | | 1.77 | | 1.02 | |
| Area near sector | 5.13 | 41% | 3.82 | 40% | 2.69 | 38% | 1.73 | 35% | 0.94 | 30% | 0.33 | 19% | 0.00 | 0% |
| Area dist sector | 6.47 | 52% | 5.08 | 53% | 3.88 | 55% | 2.86 | 58% | 2.02 | 64% | 1.37 | 78% | 1.02 | 100% |
| Area transition | 0.96 | 7.7% | 0.72 | 7.4% | 0.50 | 7.1% | 0.32 | 6.6% | 0.18 | 5.6% | 0.06 | 3.5% | 0.00 | 0% |

The IOL was also available without recessed part. This IOL was used as reference lens. It has a dioptre of +20 for the main lens part. The lens of the invention was further identical, except that it had a recessed part with a relative dioptre of +3 with respect to the main lens part. The measurement procedure above using the PMTF was used. In the table, results using a spatially "large" circular source of 600 mu diameter and a "small" source of 200 mu diameter are shown.

| Source | Small | Large | Small | Large | Small | large |
|---|---|---|---|---|---|---|
| Pupil diameter | 4.5 | 4.5 | 3.75 | 3.75 | 3.00 | 3.00 |

-continued

| Source | Small | Large | Small | Large | Small | large |
|---|---|---|---|---|---|---|
| Light in far focus | 54% | 58% | 54% | 54% | 54% | 54% |
| Light in near focus | 40% | 34% | 38% | 38% | 38% | 41% |
| Area transition | 6% | 7% | 8% | 8% | 8% | 6% |

The measured results and calculated results thus are comparable.

Figure 26:
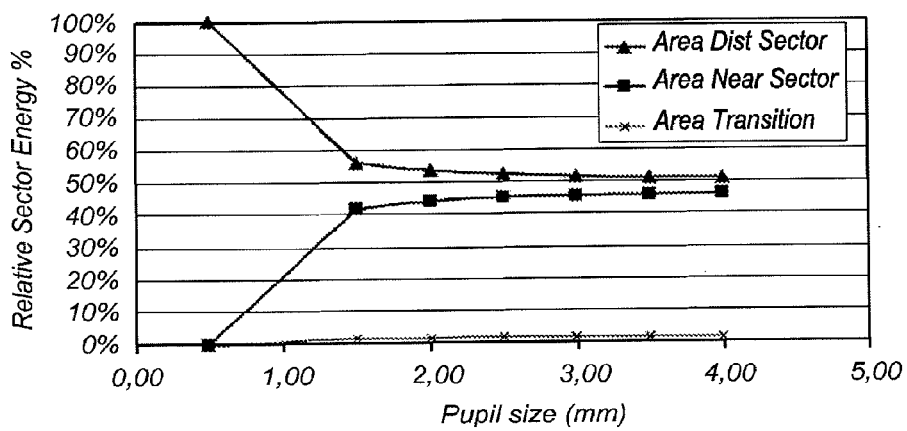

Embodiment 3, FIG. 26

| | | | | | | | | | | | | | | |
|---|---|---|---|---|---|---|---|---|---|---|---|---|---|---|
| Sector Angle Distance | | | | 182 | | | | | | | | | | |
| Sector Angle Near | | | | 170 | | | | | | | | | | |
| Sector Angle Transitions | | | | 8 | | each recess 4 degrees transition | | | | | | | | |
| Sector Radius Central | | | | 0.25 | | | | | | | | | | |
| Pupil diameter | 4.00 | 4.00 | 3.50 | 3.50 | 3.00 | 3.00 | 2.50 | 2.50 | 2.00 | 2.00 | 1.50 | 1.50 | 0.50 | 0.50 |
| Area Pupil | 12.57 | | 9.62 | | 7.07 | | 4.91 | | 3.14 | | 1.77 | | 0.20 | |
| Area near sector | 5.84 | 46% | 4.45 | 46% | 3.25 | 46% | 2.23 | 45% | 1.39 | 44% | 0.74 | 42% | 0.00 | 0% |
| Area dist sector | 6.45 | 51% | 4.96 | 52% | 3.67 | 52% | 2.58 | 53% | 1.69 | 54% | 0.99 | 56% | 0.20 | 100% |
| Area transition | 0.27 | 2.2% | 0.21 | 2.2% | 0.15 | 2.2% | 0.10 | 2.1% | 0.07 | 2.1% | 0.03 | 2.0% | 0.00 | 0% |

Figure 23:
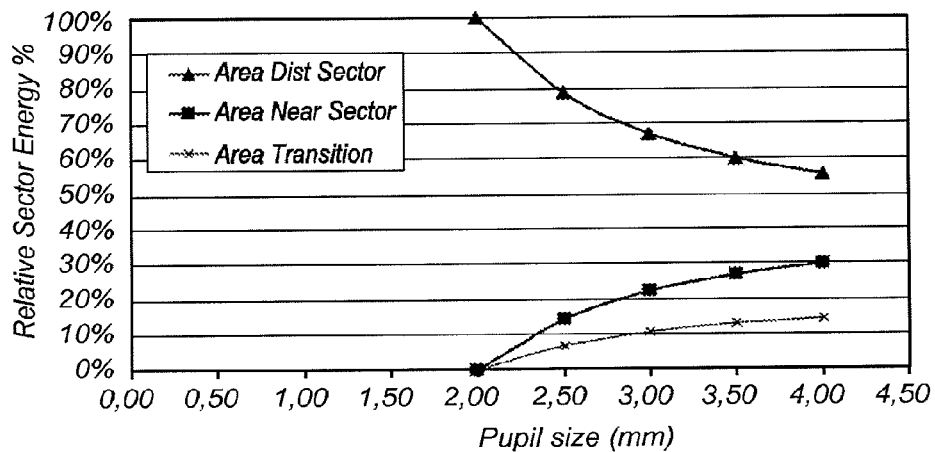

Embodiment 4, FIG. 23

| | | | | | | | | | | |
|---|---|---|---|---|---|---|---|---|---|---|
| Sector Angle Distance | | | | 145 | | | | | | |
| Sector Angle Near | | | | 145 | | | | | | |
| Sector Angle Transitions | | | | 70 | | each recess 35 degrees transition | | | | |
| Sector Radius Central | | | | 1 | | | | | | |
| Pupil diameter | 4.00 | 4.00 | 3.50 | 3.50 | 3.00 | 3.00 | 2.50 | 2.50 | 2.00 | 2.00 |
| Area Pupil | 12.57 | | 9.62 | | 7.07 | | 4.91 | | 3.14 | |
| Area near sector | 3.80 | 30% | 2.61 | 27% | 1.58 | 22% | 0.71 | 15% | 0.00 | 0% |
| Area dist sector | 6.94 | 55% | 5.75 | 60% | 4.72 | 67% | 3.85 | 79% | 3.14 | 100% |
| Area transition | 1.83 | 14.6% | 1.26 | 13.1% | 0.76 | 10.8% | 0.34 | 7.0% | 0.00 | 0.0% |

Figure 22:
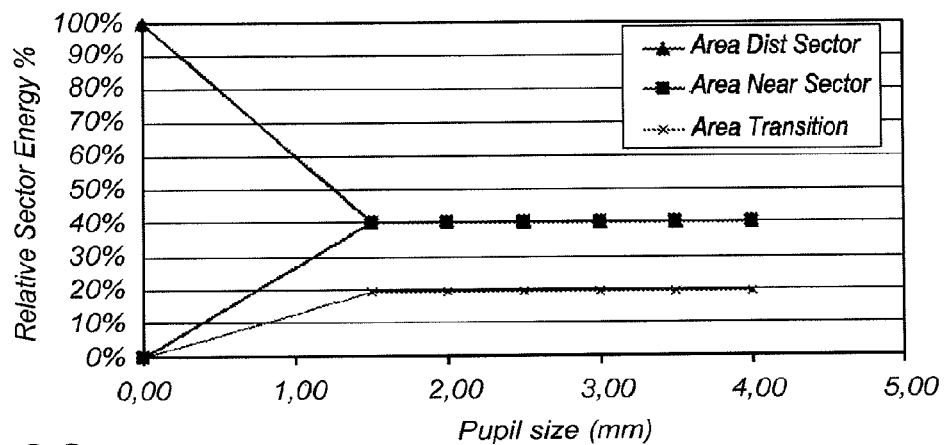

Embodiment 5, FIG. 22

|  | Sector Angle Distance | | Sector Angle Near | | Sector Angle Transitions | | Sector Radius Central | | 145 145 70 0.00 | | each recess 35 degrees transition | | | |
|---|---|---|---|---|---|---|---|---|---|---|---|---|---|---|
| Pupil diameter | 4.00 | 4.00 | 3.50 | 3.50 | 3.00 | 3.00 | 2.50 | 2.50 | 2.00 | 2.00 | 1.50 | 1.50 | 0.00 | 0.00 |
| Area Pupil | 12.57 | | 9.62 | | 7.07 | | 4.91 | | 3.14 | | 1.77 | | 0.00 | |
| Area near sector | 5.06 | 40% | 3.88 | 40% | 2.85 | 40% | 1.98 | 40% | 1.27 | 40% | 0.71 | 40% | 0.00 | 0% |
| Area dist sector | 5.06 | 40% | 3.88 | 40% | 2.85 | 40% | 1.98 | 40% | 1.27 | 40% | 0.71 | 40% | 0.00 | 100% |
| Area transition | 2.44 | 19.4% | 1.87 | 19.4% | 1.37 | 19.4% | 0.95 | 19.4% | 0.61 | 19.4% | 0.34 | 19.4% | 0.00 | 0% |

For embodiment 2, measurements were made in an Optocraft optical bench according to ISO 11979-2. In FIGS. 27-29 measurements are shown of devices having a main lens part with an optical power of +22 (FIG. 27), +29 (FIG. 28) and +15 (FIG. 29). The recessed part has a near vision part having a relative optical power (with respect to the main part) of +3.0. All the examples relate to an IOL with varying optical power of the main part. In FIG. 27, the half right below is recessed. In FIG. 28, the recessed part is upper-left, in FIG. 29, the recess is the left side. The scale is Wavefront/lambda=0.54 micron. In FIG. 27 the total scale is from −10.6 to 4.6, in FIG. 28 the scale is about −6.8 to 8.8, in FIG. 29 the scale is −12.4 to 6.3. The usual colour scale was converted to greyscale.

When manufacturing a MSIOL of the type described in this document by turning, the material removing tool usually moves parallel to the rotational axis away from and towards the work piece in a synchronised way with the angle of rotation. In this way a semi-meridian reading sector 7, 8', 20 can be created embedded or recessed in the main lens part 4. When the transition 10 is made from main lens part 4 into recessed part 7, 8 the tool and the work piece or lens have to be moved towards each other. When the transition 10 is made out of the recessed part 7, 8 to the main lens part 4, the tool and the lens have to move away from each other. When manufactured this way, a transition zone 10, 13, 13' separates the recessed part(s) from the main lens part 4. It should be clear that the dimensions of this transition zone should be as small as possible. It was found that the best results are provided if the transition zones are as small or narrow and thus as steep as possible.

To make the smallest transition zone the cutting tool and the lens should be moved towards each other and away from each other as fast as possible. Often, the tool will move with respect to the lens. Fast displacement implies the tool should be moved with the fastest acceleration allowed by the manufacturer of the cutting tool or capable by the cutting tool. The method of the present invention calculates the optimal transition profile to move the cutting tool from position 1 at rest to position 2 at rest. Position 1 corresponds to the z position of the cutting tool when processing the distance part, and position 2 corresponds to the position of the cutting tool when processing the reading part or vice versa.

If the movement of the cutting tool is limited by a specified maximum acceleration, then the fastest transition between two positions is accomplished by performing the displacement of the fast tool with this maximum acceleration during the whole transition. From simple mechanics it follows that the displacement s after applying the maximum acceleration $a_{max}$ during a time $t_1$ is:

$$s = \tfrac{1}{2} a_{max} t_1^2$$

The cutting tool will now have a speed of:

$$v = a_{max} t_1$$

To bring the fast tool back to rest v=0 we apply again the maximum acceleration on the fast tool system but now in the opposite direction. From simple mechanics it follows that the time needed to stop the fast tool $t_2$ is equal to the time that was needed to accelerate the fast tool.

$$t_2 = t_1$$

When the transition time is Δt half of the transition time is needed to accelerate the fast tool and half of the transition time is needed to bring the fast tool at rest again. From this the optimised profile that utilises the maximum allowed acceleration for the tool is given by:

$$s(t) = \tfrac{1}{2} a_{max} t^2$$

For $0 \leq t < \tfrac{\Delta t}{2}$ $$s(t) = \tfrac{1}{2} a_{max} \left(\tfrac{\Delta t}{2}\right)^2 + a_{max} \tfrac{\Delta t}{2}\left(t - \tfrac{\Delta t}{2}\right) - \tfrac{1}{2} a_{max}\left(t - \tfrac{\Delta t}{2}\right)^2$$

For $\tfrac{\Delta t}{2} \leq t \leq \Delta t$

Where Δt is the transition time.

The total and maximum displacement Δs when limited to the maximum acceleration $a_{max}$ of the fast tool is:

$$\Delta s = a_{max} \left(\tfrac{\Delta t}{2}\right)^2$$

The minimum time needed to make a displacement Δs is:

$$\Delta t = 2 \sqrt{\tfrac{\Delta s}{a_{max}}}$$

This time is the theoretical minimal time to make a displacement Δs with the cutting tool that is limited to a maximum acceleration. All other transition profiles subjected to the same limitation regarding the maximum acceleration require a larger time to make the same displacement $\Delta s$.

An important fact is that in practice to achieve a surface manufactured by turning of good quality the spindle speed is bounded to a minimum number of revolutions per minute. If the spindle speed is bounded to a minimum a smaller transition time will result in a smaller transition zone. The angular size $\phi$ in degrees of the transition zone in this case can be calculated by:

$$\phi = N \cdot 360 \cdot \Delta t$$

$$\phi = N \cdot 360 \cdot 2 \sqrt{\frac{\Delta s}{a_{max}}}$$

with N the spindle speed in revolutions per second.

Generally the height difference between the reading part and distance part decrease when moving from the periphery toward the centre of the optical zone. This implies that the angular size of the transition zone can be made smaller when approaching the centre. In this way the effective area of the optical zones is maximised. Another important advantage is that the transition is made as steep as possible this way. A steep transition can be advantageous, reflections at the transition zone are in such a way they are less or not perceived as disturbing by the patient. From this it can be concluded that with the optimised transition profile a larger displacement can be achieved for the same size of the transition profile. Or otherwise when certain amount of displacement is needed to change from distance part to reading part with the optimised transition profile this can be achieved in a faster way resulting in a smaller transition zone. A further application for the described optimised transition profile is this. To make a displacement $\Delta s$ in a time $\Delta t$ in the most controlled or accurate way it can be advantageous to make the transition with the minimum acceleration. The minimum acceleration needed to achieve a displacement $\Delta s$ in a time $\Delta t$ can be calculated with:

$$a_{min} = \frac{4\Delta s}{\Delta t^2}$$

The transition profile is given again by:

$$s(t) = \frac{1}{2} a \, t^2$$

For $0 \le t < \frac{\Delta t}{2}$ $$s(t) = \frac{1}{2} a \left(\frac{\Delta t}{2}\right)^2 + a \frac{\Delta t}{2}\left(t - \frac{\Delta t}{2}\right) - \frac{1}{2} a \left(t - \frac{\Delta t}{2}\right)^2$$

For $\frac{\Delta t}{2} \le t \le \Delta t$

Where $\Delta t$ is the transition time and a is the maximum acceleration or a specified acceleration for the most controlled transition. The above described transition starts with a horizontal slope and ends with a horizontal slope. For the case that both near and reading part zone are rotational symmetric surfaces both zones have horizontal slopes in the tangential or tool direction. In this case the zones can be connected by the transition profile in a smooth way with no discontinuity in the first derivative. In case one or both zones has or have for example non rational symmetric surfaces such as a toric surface or a decentred spherical surface, the slope will generally not be horizontal in the tool direction. To make a smooth transition in case one of the zones does not have a horizontal or zero slope in the tangential direction, the transition can be made by removing some part of the beginning or the end of the transition profile in such a way that both zones and transition zone become tangent at their point of connection. See FIG. 17. It's also not difficult to do the same analysis as above in a more generally way. That is the assumption that the tool is at rest in position 1 and in position 2 is dropped. Instead, the tool is allowed to start with a specified velocity v1 before the transition and remains at a speed v2 after the transition. The last resulting in transition profile that does optional not start or end with a horizontal slope.

Of course if one chooses it's also possible to start the transition without being tangent with one or both optical zones.

Example 1

Maximum acceleration for the cutting tool:

$a_{max}$=10 m/sec$^2$

Spindle speed 1200 rev/min (20 rev/sec) with a transition angle of 20 degrees.

$$\Delta t = \frac{1}{20} \frac{20}{360} = 2.78 \cdot 10^{-3} \text{ sec}$$

$$\frac{\Delta t}{2} = 1.39 \cdot 10^{-3} \text{ sec}$$

For $0 \le t < 1.39 \cdot 10^{-3}$: $s(t)=5t^2$
For $1.39 \cdot 10^{-3} \le t < 2.78 \cdot 10^{-3}$:
$s(t)=9.66 \cdot 10^{-6}+1.3.9 \cdot 10^{-3}(t-1.39 \cdot 10^{-3})-5(t-1.39 \cdot 10^{-3})^2$ Example 2

Spindle speed N=15 rev/sec. $\Delta s$=0.05 mm, $a_{max}$=10 m/sec$^2$ $$\Delta t = 2\sqrt{\frac{\Delta s}{a_{max}}} = 0.0045 \text{ sec}$$

$$\phi = N \cdot 360 \cdot 2 \sqrt{\frac{\Delta s}{a_{max}}} = 15 * 360 * 0.0045 = 24 \text{ degrees}$$

It's also possible to make the transition by using other less optimal profiles. For example a transition profile described by the cosine function could be used.

$s(t)=A \cdot \cos(\omega t)$

With A the amplitude and $\omega$ the angular frequency. The transition starts at $\omega$=0 and ends at $\omega=\pi$. The acceleration experienced when following this cosine profile is:

$a=-A \cdot \omega^2 \cos(\omega t)$

The maximum acceleration in the cosine profile will occur at $\omega$=0 and at $\omega=\pi$ in the opposite direction. The absolute magnitude of the acceleration is therefore:

$a_{cos\_max}=A \cdot \omega^2$

Because the maximum acceleration available or allowed for the turning machine is only used during a very small trajectory in the transition profile, the achieved displacement for the fast tool is substantially less than the described optimal transition profile in this document.

For comparison purposes, a cosine transition is calculated with the same transition time and maximum acceleration as used in the example above with the optimised transition profile (FIG. 17).

The angular frequency ω can be calculated from the transition time:

$$\omega = \frac{\pi}{\Delta t}$$

The maximum amplitude possible with maximum acceleration $a_{max}=10$ m/sec$^2$ is Distance part with radius Rd:

$$A = \frac{a_{max}}{\left(\frac{\pi}{\Delta t}\right)^2}$$

$$s(t) = A \cdot \left(1 - \cos\left(\frac{\pi}{\Delta t} t\right)\right)$$

Another function that is used to define such a transition is the sigmoid function as described in WO9716760 and U.S. Pat. No. 6,871,953. The sigmoid function is defined as (FIG. 18):

$$y(t) = \frac{1}{1 + e^{-t}}$$

If y(t) is the displacement as a function of time t, then the acceleration in the sigmoid profile (FIG. 19) is given by:

$$a = \frac{d^2 y(t)}{dt^2}$$

$$a = \frac{2e^{-2t}}{(e^{-t}+1)^3} - \frac{e^{-t}}{(e^{-t}+1)^2}$$

It shows the acceleration in the profile is not uniform. The maximum acceleration possible is not utilised during the whole transition. The speed of the transition is restricted by the extremes in the acceleration profile, see FIG. 19.

The sigmoid function can be scaled and translated to model the required transition. In the same way as shown with the cosine transition it can be easily shown that a transition that is described by a sigmoid function is less optimal. That is when limited to a maximum acceleration during the transition:

The maximum displacement in a fixed time interval is less
The time needed for a required tool displacement is larger resulting in a wider transition zone.

Rd:=10.0

$$zd(r) := Rd - \sqrt{Rd^2 - r^2}$$

Reading part with radius Rr

Rr:=8.5

$$zr(r) := Rr - \sqrt{Rr^2 - r^2}$$

Sagitta difference or height difference when moving from reading part to distance part, see FIG. 30:

saggdiff(r):=zr(r)−zd(r)

Radial distance s available to take height step when the transition is performed between two meridians that are a angle α apart at a distance r from the optical centre:

$$s(r) := 2 \cdot \pi \cdot r \cdot \frac{\alpha}{360}$$

Transition profile in the first half part $z := \frac{1}{2} \cdot a \cdot x^2$

Should be equal to half the height step $$\frac{saggdiff(r)}{2} = \frac{1}{2} \cdot a \cdot \left(\frac{s(x)}{2}\right)^2$$

$$a := \frac{saggdiff(r)}{\left(\frac{s(x)}{2}\right)^2}$$

$$a := \frac{4 \cdot saggdiff(r)}{s(x)^2}$$

$$a := 4 \cdot \frac{\left[Rr - \sqrt{Rr^2 - r^2}\right] - \left(Rd - \sqrt{Rd^2 - r^2}\right)}{\left(2 \cdot \pi \cdot r \cdot \frac{\alpha}{360}\right)^2}$$

Slope half way the transition profile:

$$slope := \left[\frac{d}{dx}\left(\frac{1}{2} \cdot a \cdot x\right)^2\right]$$

$$slope := a \cdot x$$

$$slope := a \cdot \frac{\left(2 \cdot \pi \cdot r \cdot \frac{\alpha}{250}\right)}{2}$$

$$slope(r) := 4 \cdot \frac{\left[Rr - \sqrt{Rr^2 - r^2}\right] - \left(Rd - \sqrt{Rd^2 - r^2}\right)}{\left(2 \cdot \pi \cdot r \cdot \frac{\alpha}{360}\right)^2} \cdot \frac{\left(2 \cdot \pi \cdot r \cdot \frac{\alpha}{360}\right)}{2}$$

$$slope(r) := \frac{\left[Rr - \sqrt{Rr^2 - r^2}\right] - \left(Rd - \sqrt{Rd^2 - r^2}\right)}{\left(\pi \cdot r \cdot \frac{\alpha}{360}\right)}$$

See FIG. 32, showing a graph of the slope or first derivative of the steepest part of the blending part as a function of the radial distance from the optical centre of the ophthalmic lens, for a blending zone between two semi meridian lines enclosing an angle of 15 degrees, and FIG. 32, for a blending part enclosed by two semi meridians enclosing an angle of 4 degrees. Below, several values are shown in a table

| Distance | slope 15 deg | slope 4 deg |
|---|---|---|
| 0.4 | 0.027 | 0.101 |
| 0.8 | 0.054 | 0.203 |
| 1.2 | 0.082 | 0.307 |
| 1.6 | 0.11 | 0.414 |
| 2.0 | 0.14 | 0.524 |
| 2.4 | 0.171 | 0.64 |
| 2.8 | 0.203 | 0.761 |

The shape and slope (first derivative) of the blending zone can be measured with high accuracy, using for instance a 3D Optical Profiler or Form talysurf, commercial available from Taylor Hobson, the United Kingdom. FIG. 35 shows a surface map of a lens according to the invention.

It was found in clinical trials that with a steep slope and careful choice of central part, the contrast of the lens increases. In a recent performed European multicentric clinical study (Pardubice study data on file), 25 subjects with 49 eyes, 24 subjects were bilateral implanted with the inventive MSIOL. These subjects represent a sample selection of the population of typical European cataract patients. The contrast sensitivity was measured under photopic conditions with a CSV1000 instrument from Vector Vision Inc, Greenville, Oh., USA U.S. Pat. No. 5,078,486. In this study the following LogMar (Logarithmic Mean Angle Resolution) values, measured with the CSV1000, where found for spatial frequencies 3, 6, 12 and 18 cpd:

| spatial frequency (cpd) 3 months | StDev |
| --- | --- |
| 3 | 1.677 +/− 0.15 |
| 6 | 2.073 +/− 0.17 |
| 12 | 1.831 +/− 0.21 |
| 18 | 1.437 +/− 0.19 |

A contrast sensitivity comparison was made with the two market leaders in MIOL. The AcrySof ReSTOR SN60D3 (Alcon) is a refractive/diffractive MIOL and the ReZoom (Advanced Medical Optics) is a multizone refractive multifocal aiming improved visual outcome.

In a recent study titled "Multifocal Apodized Diffractive IOL versus Multifocal Refractive IOL" published in the Journal Cataract Refract Surg 2008; 34:2036-2042 Q 2008 ASCRS and ESCRS, contrast sensitivity was measured in 23 patients who had bilateral implantation of the AcryS of ReSTOR SN60D3 IOL and 23 patients who had bilateral implantation of the ReZoom IOL. The number of subjects in our study was 24 and therefore direct comparable with the outcome of this study. It shows a mean contrast sensitivity improvement of at least 25% compared with a state of the art concentric refractive multifocal lens. The inventive lens configuration will give a mean contrast sensitivity for healthy eyes (1.677) at 3 cpd, (2.07) at 6 cpd, (1.831) at 12 cpd and (1.437) at 18 cpd. In FIGS. 33 and 34, the results are indicated when compared to the performance of an average population, for several age groups (Pop. Norm http://www.vectorvision.com/html/educationCSV1000Norms.html), the performance of the test group before surgery (pre-op), and the performance with an MIOL indicated as LS 312-MF. These results were found consistent at 6 months post operative, i.e., 6 months after surgery.

It will also be clear that the above description and drawings are included to illustrate some embodiments of the invention, and not to limit the scope of protection. Starting from this disclosure, many more embodiments will be evident to a skilled person which are within the scope of protection and the essence of this invention and which are obvious combinations of prior art techniques and the disclosure of this patent.

The invention claimed is:

1. An intra-ocular lens comprising opposing first and second sides, and
    a main lens part having a surface at the first side and an optical axis passing through an optical centre of the intra-ocular lens, the main lens part having an optical power;
    a recessed part having a surface at the first side, which surface is recessed with respect to the surface of the main lens part, the surface of the recessed part having at least one boundary with the surface of the main lens part and the recessed part comprising a near vision part, the near vision part having an add power with respect to the optical power of the main lens part;
    a central part having a surface at the first side, which surface is arranged such as to have boundaries with the surface of the main lens part and the surface of the recessed part, the central part having a relative optical power with respect to the optical power of the main lens part;
    wherein the central part is circular with a diameter between about 0.5 and 3.0 mm; and
    wherein the surface of the recessed part is shaped as a meridian zone having a boundary with the surface of the main lens part, the boundary comprising two semi meridians passing over the surface of the main lens part and through the optical centre.

2. The lens according to claim 1, wherein the central part comprises the optical centre.

3. The lens according to claim 1, wherein the relative optical power of the central part with respect to the optical power of the main lens part is between 0% and 100% of the relative optical power of the near vision part with respect to the optical power of the main lens part.

4. The lens according to claim 1, wherein the relative optical power of the central part is between about −2.0 and +2.0 dioptre with respect to the optical power of the main lens part.

5. The lens according to claim 1, wherein the central part is circular with a diameter between about 0.5 and 2.0 mm.

6. The lens according to claim 1, wherein the surface of the recessed part is bounded by a line of latitude, which is concentric with and at a distance from the central part in the radial direction with respect to the optical axis.

7. The lens according to claim 1, wherein the main lens part is configured for distance vision.

8. The lens according to claim 1, wherein the near vision part is configured for reading vision.

9. The lens according to claim 1, wherein the near vision part has a relative optical power of about +1.0 to about +5.0 dioptre with respect to the optical power of the main lens part.

10. The lens according to claim 1, wherein the near vision part has a relative optical power of about +1.5 to about +4.0 dioptre with respect to the optical power of the main lens part.

11. The lens according to claim 1, wherein the main lens part has an optical power of about −20 to about +35 dioptre.

12. The lens according to claim 1, wherein the main lens part has an optical power of about −10 to about +30 dioptre.

13. An intra-ocular lens comprising
    a main lens part having a curvature radius Rv;
    a circular central part having a first optical property and having a diameter between about 0.5 and 2 mm; and
    a meridian part comprising a recess which is bounded by the circular central part, by two meridians passing through a centre of the central part, and by a lower boundary which is concentric with respect to the circular part, the meridian part forming a recess in the lens, the recess having an outer limit lying on or within the curvature radius Rv, and the meridian part comprising a reading vision part.

14. An oculary supported multifocal intra-ocular lens provided with a circular central lens portion having a diameter between about 0.5 and 2 mm;
a lower lens portion in a lower lens part of the multifocal lens neighbouring the central lens portion; and
a further lens portion having a curvature radius Rv,
wherein the lower lens portion comprises a recess comprising two sides which run from the central lens portion towards a rim of the multifocal lens, and an outer limit of the lower lens portion lies on or within an imaginary sphere having its origin and radius of curvature coinciding with the curvature radius Rv of the further lens portion.

15. The lens according to claim 1, wherein the central part is circular with a diameter between about 0.6 and 3.0 mm.

16. The lens according to claim 1, wherein the central part is circular with a diameter between about 0.8 and 3.0 mm.

17. The lens according to claim 1, wherein the central part is circular with a diameter between about 0.8 and 2.0 mm.

* * * * *